US012046360B2

(12) United States Patent
Kogan et al.

(10) Patent No.: US 12,046,360 B2
(45) Date of Patent: Jul. 23, 2024

(54) SYSTEM AND METHOD FOR OPTIMIZING HOME VISIT APPOINTMENTS AND RELATED TRAVEL

(71) Applicants: Daniel Kogan, Brooklyn, NY (US); Rada Sumareva, New York, NY (US); Gennady Ukrainksy, New York, NY (US)

(72) Inventors: Daniel Kogan, Brooklyn, NY (US); Rada Sumareva, New York, NY (US); Gennady Ukrainksy, New York, NY (US)

(73) Assignee: ZIPHYCARE INC, New York, NY (US)

( * ) Notice: Subject to any disclaimer, the term of this patent is extended or adjusted under 35 U.S.C. 154(b) by 202 days.

(21) Appl. No.: 17/848,419

(22) Filed: Jun. 24, 2022

(65) Prior Publication Data
US 2023/0005607 A1 Jan. 5, 2023

Related U.S. Application Data

(60) Provisional application No. 63/214,956, filed on Jun. 25, 2021.

(51) Int. Cl.
*G16H 40/20* (2018.01)
*G01C 21/36* (2006.01)
(Continued)

(52) U.S. Cl.
CPC ......... *G16H 40/20* (2018.01); *G01C 21/3617* (2013.01); *G01C 21/3691* (2013.01);
(Continued)

(58) Field of Classification Search
CPC ....... G06Q 10/1095; G06Q 10/063116; G06Q 10/1093; G06Q 10/1097; G06Q 10/06311;
(Continued)

(56) References Cited

U.S. PATENT DOCUMENTS

2013/0253339 A1* 9/2013 Reyes .................... G06Q 10/06
600/549
2017/0147762 A1* 5/2017 Vallee .................... G16Z 99/00
(Continued)

FOREIGN PATENT DOCUMENTS

AU 2018102165 A4 2/2018
WO 2016127918 A1 8/2016

OTHER PUBLICATIONS

Arnaud Laurent, Nathalie Klement; "Bin Packing Problem with priorities and incompatibilities using PSO: application in a health care community"; 9th IFAC Conference on Manufacturing Modelling, Management and Control; Aug. 2019, pp. 2744-2749; Berlin, Germany.

*Primary Examiner* — Joseph D Burgess
(74) *Attorney, Agent, or Firm* — Ashok Tankha

(57) ABSTRACT

A system and a computer-implemented method employ an appointment optimization and route planning system (AORPS) for optimizing home-visit appointments and related travel for delivering patient care. The AORPS receives registration and patient data from patients and client input including information about healthcare providers, onsite care coordinators, health plans, appointment types, and success rates from a client. The AORPS collates the patient data and generates an input matrix from the client input and the collated patient data. The AORPS generates a predictive model for appointments, capitation, and return on investment for delivering patient care based on appointment and patient history, feedback, and healthcare data. The AORPS generates an appointment schedule with travel routes dynamically based on optimization factors derived from the client input, the collated patient data, the input matrix, the healthcare data, and the predictive model, incor-
(Continued)

porating real-time changes in patient data, the client input, the optimization factors, and appointments.

20 Claims, 6 Drawing Sheets

(51) Int. Cl.
*G16H 10/60* (2018.01)
*G16H 50/20* (2018.01)

(52) U.S. Cl.
CPC ......... *G01C 21/3697* (2013.01); *G16H 10/60* (2018.01); *G16H 50/20* (2018.01)

(58) Field of Classification Search
CPC ....... G06Q 10/06316; G06Q 10/06312; G06Q 10/06; G06Q 10/0631; G06Q 10/10; G16H 10/60; G16H 40/20; G16H 80/00
See application file for complete search history.

(56) References Cited

U.S. PATENT DOCUMENTS

| | | |
|---|---|---|
| 2017/0286622 A1 | 10/2017 | Corporation |
| 2020/0078950 A1 | 3/2020 | Fernando et al. |
| 2021/0090721 A1 | 3/2021 | Funk et al. |

* cited by examiner

SYSTEM AND METHOD FOR OPTIMIZING HOME VISIT APPOINTMENTS AND RELATED TRAVEL

CROSS-REFERENCE TO RELATED APPLICATIONS

This application claims priority to and the benefit of the provisional patent application titled "System and Method for Optimizing Home Visit Appointments and Related Travel", application No. 63/214,956, filed in the United States Patent and Trademark Office on Jun. 25, 2021. The specification of the above referenced patent application is incorporated herein by reference in its entirety.

BACKGROUND

Clinically complex patients who are home-bound and/or live in remote areas require continuous care, but face tremendous barriers to accessing quality medical services, complying with treatment plans, staying on track with prescribed medications, and sustaining behaviors that support well-being. When patients do not receive the right kind of care, their health suffers, they wind up in an emergency room (ER) or are hospitalized, and insurance providers' costs skyrocket. In the United States of America (USA), 15% of its annual gross domestic product (GDP) is spent on healthcare. This equates to more than about $3 trillion per annum or over about $10,000 per person. Eighty percent of the country's expenditure is spent on behalf of 20% of its sickest population, that is, chronically ill and aging patients with complex medical conditions including, for example, diabetes, congestive heart failure, and respiratory diseases.

To stem rising healthcare costs as a percentage of its GDP, the United States (U.S.) Government shifted the burden of healthcare costs from individuals, prior to 1950, to third party payers, hereinafter referred to as payers, including the government through programs such as Medicare, Medicaid, and the military health care system, and the private sector, for example, through managed care systems. Typically, a private sector entity seeks a profit margin of 2% in Medicaid and 15% in Medicare and, in order to control its medical expenditures, must effectively manage the 20% of its members with complex, chronic conditions. Over the past several decades, payers have experimented with, and failed at, programs such as disease management, case management, avoidance of emergency rooms, and avoidance of preventable hospital admissions. Payers have struggled to provide quality care, universal access to care, and cost-effective care due to continually rising costs in the hospital and pharmacy sectors of the marketplace. Payers have attempted to extend the reach of cost-effective care to nurse hot-lines, walk-in clinics, urgent care centers, doctor house calls, and most recently, telehealth. However, none have proven to be the Holy Grail of cost-effective healthcare because they have been unable to make a significant impact on the 20% of patients with 80% of the costs, whose barriers to care include lack of finances, lack of access, lack of compliance, poor healthcare choices such as smoking and obesity, and inability to overcome psychosocial issues that impact health and longevity.

$800 billion is spent each year in the U.S. on Medicare recipients. $250 billion of that cost is spent by Medicare Advantage plans with a total membership of 3.5 million patients. There are more than 3,500 Medicare Advantage plans operating in the U.S., although 80% of that market is controlled by eight of the largest national and regional health plans. There is an unmet need for care of the neediest population who live in subsidized housing throughout major cities in the U.S. Underserved communities house the fastest growing and costliest populations, that is, seniors, in the country. Seniors have twice the level of chronic illness than the general population with 60% greater behavioral comorbidities and corresponding gaps in care. There is a need for cost-effective, quality care among the neediest patient populations.

Moreover, ongoing and rapid growth has occurred in state government assist programs in the managed care market in the form of "Managed Long Term Care" (MLTC). Patients who require managed long term care are home-bound and require low-level personal care assistance with their daily activities. There has also been growth in the need for primary care in the "Skilled Nursing Facility" (SNF) market since skilled nursing facilities (SNFs) are a well-known nidus for repeated and frequent hospitalizations due to a paucity of care at those facilities. This has promulgated a growth in new companies providing primary care to nursing home patients but without resources to manage the entirety of this growing sector of the market. The growth in both MLTC and SNF healthcare needs have further demonstrated the need for a model of care which is entirely scalable to MLTC and SNF care.

The largest growth sector in the U.S. has been in the population over the age of 65. Driven by the aging of the "baby boomers" generation, this demographic sector grew by over a third during the past decade, and by about 3.2%, that is, about 1,688,924, from the year 2018 to the year 2019. In addition to the aging of the population, there has been an increasing trend of chronic illnesses such as obesity and diabetes in the U.S. For example, the prevalence of diagnosed diabetes increased from 0.93% of the population in the year 1958 to 7.40% in the year 2015. The U.S. economy grew exponentially from 2017 through the beginning of 2020. Despite the negative impact on the economy as a result of the Coronavirus disease (COVID-19) pandemic, the U.S. economy is rebounding. Certain sectors of the economy continue to surge as a direct result of COVID-19. Additional forces driving upward growth in the health technology market has been the continuous downward pressure on Medicare and Medicaid premiums from both federal and state governments. Managed care plans in these sectors have seen continued erosion into their profit margins. Medicare Advantage plans have seen additional ceilings in their profitability as a result of a capping of their medical loss ratios, with no counter-balancing floor on their losses. As a result, entities in the healthcare space are searching for new and cost-effective ways to reduce the high costs of emergency room (ER) usage, hospital admissions, and pharmacy. The single largest driver of remote and at-home healthcare services has been the COVID-19 pandemic. As a result of voluntary and mandatory confinements during the height of the pandemic, healthcare delivery had become even less accessible and patients were dying from other diseases due to a lack of treatment and psychosocial factors dramatically increasing the risk of death due to heart disease, cancer, and suicides. Federal and local governments mandated payments for telehealth. Managed care payers have tried to expand home health visits. As a result, the public has a growing introduction and greater experience with remote care and has turned to remote care as an alternative to a doctor or emergency room visit.

Due to high cost and lack of coordination of house calls, inadequate technology of telehealth, and general failures of disease management companies, telehealth solutions have been wanting. Spurred by the high cost of utilization and COVID-19, many entities have entered the remote, care-at-home, market. The growth of this market, due to COVID-19 becoming covered expenses, increases the need for care-at-home services as patients get exposed to the availability of such services. The general public has always embraced home healthcare. However, remote healthcare had greatly lagged and was either not well-accepted by patients and/or was not a covered expense by payers. Since the advent of the COVID-19 pandemic, acceptance of remote healthcare by the general public has increased dramatically. Use of telehealth, for example, is now commonplace and a covered benefit for Medicare and health plans and payment has been mandated by federal and local legislatures and executive orders.

As an example of the need for a medical solution, it is estimated that 25% of Medicare patients are chronically affected by diabetes and 10% of those patients have complex, comorbid conditions that are poorly controlled. In the Medicare Advantage sector alone, this represents an estimated target of 80,000 members in need of an appropriate medical solution in the New York (NY) tri-state area for diabetes alone. This patient population generates the highest cost to insurance providers due to non-compliance with prescribed medical, social, and behavioral protocols which results in recurring emergency room (ER) visits and re-hospitalization.

Hence, there is a long-felt need in the healthcare industry for an at-home evaluation, management, and emergency room diversion system and method that optimizes home-visit appointments and related travel for delivering superior patient care as well as significant savings to health insurance providers.

Furthermore, there is a long-felt need in the healthcare industry for a healthcare solution that bridges the divide between clinical primary care and managed care case management. Furthermore, there is a long-felt need for a healthcare model that provides real-time data on utilization, quality, and cost. Furthermore, there is a long-felt need for collection of medical and psychosocial data and to enhance machine learning (ML) algorithms that analyze and predict future population risks and cost-saving opportunities in any given geography.

Furthermore, there is a long-felt need in the healthcare industry for a healthcare solution that improves patient compliance, satisfaction, and health outcomes, that removes barriers to healthcare and closes gaps in quality, that reduces emergency room visits and in-patient admissions and re-admissions, that increases patient, physician, and health insurance company satisfaction, and that achieves the elusive goal of cost-effective, quality care among patient populations that generate some of the highest costs incurred by healthcare companies.

SUMMARY OF THE INVENTION

This summary is provided to introduce a selection of concepts in a simplified form that are further disclosed in the detailed description of the invention. This summary is not intended to determine the scope of the claimed subject matter.

The system and the computer-implemented method disclosed herein address the above-recited needs for an at-home evaluation, management, and emergency room diversion system and method that optimizes home-visit appointments and related travel for delivering superior patient care as well as significant savings to health insurance providers while capturing real-time data on utilization, quality, and cost. The system and the computer-implemented method provide a healthcare solution that improves patient compliance, satisfaction, and health outcomes, that removes barriers to healthcare and closes gaps in quality, that reduces emergency room visits and in-patient admissions and re-admissions, that increases patient, physician, and health insurance company satisfaction, and that achieves the elusive goal of cost-effective, quality care among patient populations that generate some of the highest costs incurred by healthcare companies. Moreover, the system and the computer-implemented method employ machine learning (ML) and artificial intelligence (AI) algorithms that analyze and predict future population risks and cost-saving opportunities in any given geography. The system and the computer-implemented method manage delivery of medical care through a comprehensive, continuous, coordinated, and technologically advanced system delivered to the most complex, costly, and chronically ill patients, extending the reach of an overburdened healthcare delivery system. The system and the computer-implemented method employ technology to bridge the gaps between patients, primary and specialty care, and third-party payers in the government and private sectors and focuses on healthcare value comprising access, care management/coordination, member compliance/adherence, and closing quality care gaps. The system and the computer-implemented method also employ technology to bridge the divide between clinical primary care and managed care case management. The system and the computer-implemented method manage patient care that focuses on continuity, coordination, and integration of care by blending medical, psychosocial, and behavioral care, bridging primary care with case management, and improving telemedicine. The system and the computer-implemented method employ leading edge technology to bring patient care into the home and areas remote from typical brick and mortar facilities.

The system and the computer-implemented method disclosed herein provide a remote examination experience that approximates a doctor-present exam by providing a telemedicine scenario in which physicians not only see and hear patients remotely, but also conduct in-depth screenings and exams using hospital-grade, United States Food and Drug Administration (FDA)-registered diagnostic equipment deployed by trained onsite care coordinators (OCCs) acting as the "physician's hands" at a patient location. The remote examination experience integrates the behavioral, social, and medical components of healthcare. The system and the computer-implemented method collect data in real time, measure trends using a predictive model, initiate solutions to reverse negative trends using machine learning and artificial intelligence algorithms, and optimize capitation models for healthcare providers and insurance providers. In separate embodiments, the system and the computer-implemented method provide a remote, high-touch patient examination mode where doctors, who are part of the healthcare providers, view data from a patient's location in real time through a telehealth bridge from their offices to a telehealth kit at the patient's location; and a telehealth mode where real-time data is not necessary, for example, for follow-ups, prescription refills, and routine check-ins. For example, chronic care management (CCM) programs include a mix of the remote, high-touch patient examination mode and the telehealth mode that work together to utilize and optimize available resources based on a patient's needs. A patient-care solution that merely uses telehealth is not the same as the real physical data collected in real time during at-home or onsite visits, which is an integral part of the system and the computer-implemented method disclosed herein.

The system and the computer-implemented method disclosed herein provide a proprietary appointment scheduling system that maximizes provider capacity across locations using proprietary algorithms. In effect, this allows one doctor to make multiple home visits concurrently. The system and the computer-implemented method collect medical and psychosocial data configured to be used in machine learning algorithms for analyzing and predicting future population risks and cost-saving opportunities. Given the fixed costs of hospitalization and re-hospitalization of patients with chronic conditions, emergency room (ER) visits, and an overall 80% budget spent on the population that uses ERs as the primary care, in an embodiment, the system and the computer-implemented method compute return on investment (ROI) by comparing a cohort of patients using the system to a few slices of similar cohorts from the same or even different plans, and clustering by similar age, conditions, and other social determinants of health. Given the cohort of patients, the system and the computer-implemented method create a home-visit appointment schedule according to the risk, among other factors, and attempts to cover visits to the most critical patients first, reducing unnecessary burden on the health system.

The system and the computer-implemented method disclosed herein employ an appointment optimization and route planning system (AORPS) that defines computer program instructions executable by at least one processor for optimizing home-visit appointments and related travel for delivering patient care. The processor(s) is communicatively coupled to a non-transitory, computer-readable storage medium configured to store the computer program instructions and data defined and collected by the AORPS. Moreover, the system disclosed herein comprises one or more appointment scheduling modules, a global navigation satellite system (GNSS) module and a mapping module. The mapping module is configured to receive location input from the GNSS module. In an embodiment, the mapping module is a mapping module. The AORPS optimizes home-visit appointments and related travel for delivering patient care using algorithms comprising, for example, one or more of decision trees, machine learning models, and regression models.

The appointment optimization and route planning system (AORPS) receives registration data and patient data from patients. The AORPS also receives client input comprising, for example, information about healthcare providers and onsite care coordinators such as their hours of availability; health plan commitments; appointment types; and a success rate of operation, from a client. The client is, for example, an administrator of a healthcare company that coordinates with the healthcare providers and the onsite care coordinators for the home-visit appointments. The AORPS receives the registration data and the patient data from the patients and the client input from the client through the appointment scheduling modules via a network, for example, the internet. The AORPS provides a user interface, for example, a web interface or a mobile application (app) interface, on the appointment scheduling modules for the patients and the client to input data depending on an electronic device used by the patients and the client to communicate with the appointment scheduling modules via the network. The AORPS collates the received patient data to capture information, for example, about the patients' addresses, comorbidities, social and/or psychosocial determinants of health, religious beliefs, family status, gender, communities to which the patients belong, outstanding traits, insurance plans, insurance plan needs, and other relevant data in accordance with standard ontologies of health-related information for delivering relevant patient care, for clustering similar patients, and for matching appropriate healthcare providers and onsite care coordinators to each patient.

The appointment optimization and route planning system (AORPS) generates an input matrix based on the client input and the collated patient data, covering a preconfigured period of time, for example, thirty days. The input matrix comprises, for example, schedules of the healthcare providers and the onsite care coordinators, patient cohorts, expected minimum daily and maximum monthly volumes of appointments, and success rates of the appointments. The AORPS generates a predictive model for appointments, capitation, and return on investment for delivering patient care based on training data comprising, for example, appointment history, patient history, feedback, and healthcare data. The AORPS generates an appointment schedule with travel routes via the mapping module, which communicates with the global navigation satellite system module to map out the travel routes as determined by the AORPS. The AORPS generates the appointment schedule with the travel routes dynamically based on optimization factors derived from the received client input, the collated patient data, the generated input matrix, the healthcare data, and the generated predictive model, incorporating real-time changes in the patient data, the client input, the optimization factors, and appointments. In an embodiment, the AORPS assigns a mode of appointment comprising a remote, high-touch patient examination mode or a telehealth mode to each of the appointments in the generated appointment schedule based on the optimization factors.

In an embodiment, the system disclosed herein comprises a client device configured for use by the client to communicate with the appointment scheduling modules via a network. The appointment optimization and route planning system (AORPS) sends the generated appointment schedule with the travel routes to the client and relevant appointment information from the appointment schedule to corresponding patients through the appointment scheduling modules. Furthermore, the AORPS receives changes, if any, in the patient data and the client input, and responses and requests pertaining to the appointments from the client and the patients through the appointment scheduling modules. The AORPS communicates with the patients and the client through the appointment scheduling modules using the user interface of the appointment scheduling modules.

The patient data that the appointment optimization and route planning system (AORPS) receives from the patients comprises, for example, age, gender, profession, location, lists of chronic health conditions, medical history, healthcare programs enrolled by the patients such as urgent care on demand, a primary care provider (PCP) program, and/or a chronic conditions management (CCM) program, free-form self-reports about current health, and reasons for requiring medical attention. The patient data further comprises, for example, preferred time bounds to interact with one or more of the healthcare providers and the onsite care coordinators, and payment information. While receiving the patient data from the patients through the user interface of the appointment scheduling modules, the AORPS matches input from the patients with standard ontologies of health-related information in real time to provide input suggestions to the patients. The AORPS receives the feedback in the training data, one of the factors based on which the AORPS generates the predictive model, from the patients, the client, the healthcare providers, and the onsite care coordinators through the user interface of the appointment scheduling modules via a network. The healthcare data, another one of the factors based on which the AORPS generates the predictive model, comprises, for example, healthcare information of cohorts similar to the patients in terms of demographics and comorbidities, costs of healthcare implementations in a country, and insurance information.

The predictive model generated by the appointment optimization and route planning system (AORPS) comprises, for example, predicted patient behaviors, suggested cadence of appointments for each of the patients, predicted equipment requirements, appointment cancellation probabilities for each of the patients, potential outcomes, expected costs, capitation projections for insurance plans, return on investment for the insurance plans, and clusters of patients based on each of the collated patient data, the client input, the feedback in the training data, social and psychosocial determinants of health of the patients, insurance plans of the patients, and insurance plan needs of the patients. In an embodiment, the AORPS utilizes one or more of decision trees, machine learning models, and regression models for generating and executing the predictive model and for generating the appointment schedule. Furthermore, the AORPS dynamically adjusts the generated appointment schedule with the travel routes in real time based on changes in the optimization factors, changes in the patients, changes in the healthcare providers and the onsite care coordinators, and rejection of appointments by the patients with minimal disruption.

In one or more embodiments, related systems comprise circuitry and/or programming for executing the methods disclosed herein. The circuitry and/or programming comprise one or any combination of hardware, software, and/or firmware configured to execute the methods disclosed herein depending upon the design choices of a system designer. In an embodiment, various structural elements are employed depending on the design choices of the system designer.

BRIEF DESCRIPTION OF THE DRAWINGS

The foregoing summary, as well as the following detailed description of the invention, is better understood when read in conjunction with the appended drawings. For illustrating the embodiments herein, exemplary constructions of the embodiments are shown in the drawings. However, the embodiments herein are not limited to the specific components, modules, and methods disclosed herein. The description of a component, or a module, or a method step referenced by a numeral in a drawing is applicable to the description of that component, or that module, or that method step shown by that same numeral in any subsequent drawing herein.

DETAILED DESCRIPTION OF THE INVENTION

Various aspects of the disclosure herein are embodied as a system, a method, or a non-transitory, computer-readable storage medium having one or more computer-readable program codes stored thereon. Accordingly, various embodiments of the disclosure herein take the form of an entirely hardware embodiment, an entirely software embodiment comprising, for example, microcode, firmware, software, etc., or an embodiment combining software and hardware aspects that are referred to herein as a "system", a "module", an "engine", a "circuit", or a "unit".

Figure 1:
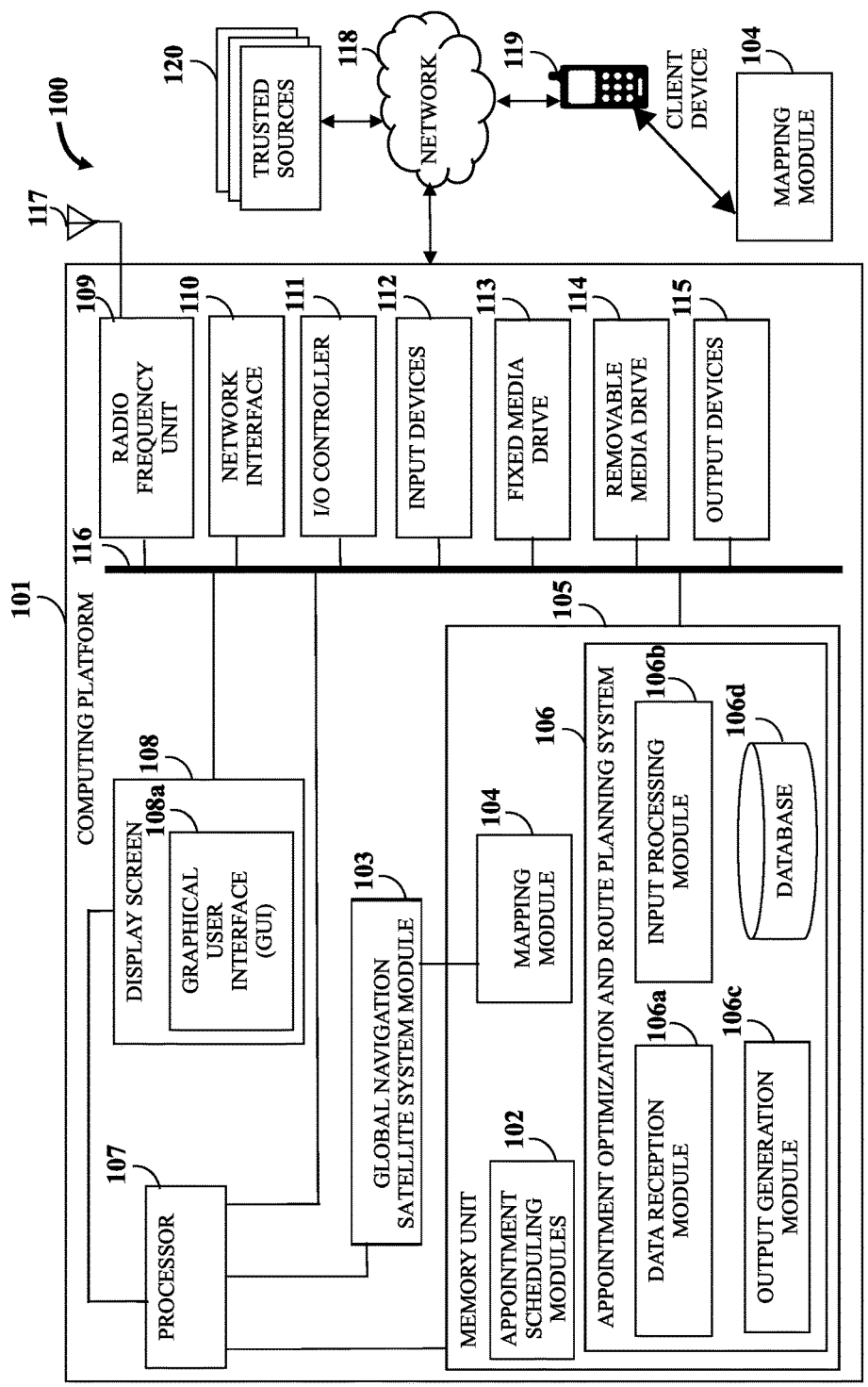
FIG. 1 illustrates an architectural block diagram of an exemplary implementation of a system for optimizing home-visit appointments and related travel for delivering patient care.

FIG. 1 illustrates an architectural block diagram of an exemplary implementation of a system 100 for optimizing home-visit appointments and related travel for delivering patient care. The system 100 disclosed herein comprises a computing platform 101 with one or more appointment scheduling modules 102, a global navigation satellite system (GNSS) module 103, a mapping module 104, and hardware components typically found in an electronic device including input/output devices, processors, storage units, and communication devices. In an embodiment, the computing platform 101 implements server-side technology supporting web modules and mobile application modules. In an embodiment as exemplarily illustrated in FIG. 1, the mapping module is a mapping module 104 configured to receive location input from the GNSS module 103. In an embodiment, the appointment scheduling modules 102 and the mapping module 104 are implemented in software that runs on hardware in the computing platform 101. The GNSS module 103 is a satellite navigation device, for example, a global positioning system (GPS) unit. The GNSS module 103 may provide location information to a web mapping service such as Google Maps®, Apple Maps, etc., for determining location, planning routes, etc. The system 100 further comprises an appointment optimization and route planning system (AORPS) 106 implemented on the computing platform 101. In other embodiments, the appointment scheduling modules 102 are implemented as servers that are strategically located to be geographically close to users communicating with them to provide quick response times, for example, in cases of sensitive and real-time data communication. In other embodiments, the mapping module 104 is a separate electronic device with navigation software and map data akin to some commercially available systems, for example, the Garmin® MAP PILOT system, that connects to the global navigation system module 103 and the Internet. In an embodiment, the mapping module 104 is implemented as a mobile application on the client device 119 and provides a mobile application (app) interface as a graphical user interface or other user interface on the client device 119 to allow the client to communicate with the appointment scheduling modules 102.

In an embodiment, the computing platform 101 is a single computing device with attached peripheral devices and other electronic subsystems such as the global navigation satellite system (GNSS) module 103. The computing device is, for example, a personal computer, a tablet computing device, a mobile computer, a portable computing device, a laptop, a touch device, a workstation, a server, a portable electronic device, a network-enabled computing device, an interactive network-enabled communication device, any other suitable computing equipment, combinations of multiple pieces of computing equipment, etc. In an embodiment, the computing equipment is used to implement applications such as media playback applications, a web browser, an electronic mail (email) application, a calendar application, mobile applications, etc., with one or more servers associated with one or more online services. In other embodiments, the computing platform 101 is made up of separate computing devices including servers, desktop computers, mobile computers, hand-held electronic devices, and wearable electronic devices along with attached peripheral devices and other electronic subsystems such as the GNSS module 103 distributed over different locations and interconnected via a network 118, for example, a short-range network or a long-range network.

The network 118 is, for example, the internet, an intranet, a wired network, a wireless network, a communication network that implements Bluetooth® of Bluetooth Sig, Inc., a network that implements Wi-Fi® of Wi-Fi Alliance Corporation, an ultra-wideband communication network (UWB), a wireless universal serial bus (USB) communication network, a communication network that implements ZigBee® of ZigBee Alliance Corporation, a general packet radio service (GPRS) network, a mobile telecommunication network such as a global system for mobile (GSM) communications network, a code division multiple access (CDMA) network, a third generation (3G) mobile communication network, a fourth generation (4G) mobile communication network, a fifth generation (5G) mobile communication network, a long-term evolution (LTE) mobile communication network, a public telephone network, etc., a local area network, a wide area network, an internet connection network, an infrared communication network, etc., or a network formed from any combination of these networks. In various embodiments, the network 118 is a wired network, or a wireless network, or a combination of networks using different protocols. In an embodiment, the appointment optimization and route planning system (AORPS) 106 is accessible to users, for example, patients, clients, healthcare providers, and onsite care coordinators availing services of the AORPS 106 through a broad spectrum of technologies and devices such as cellular phones, tablet computing devices, etc., with access to the network 118. The system 100 further comprises a client device 119 configured for use by each client to communicate with the appointment scheduling modules 102 via the network 118. The client is, for example, an administrator of a healthcare company that coordinates with healthcare providers and onsite care coordinators for scheduling the home-visit appointments. The AORPS 106 provides a web interface or a mobile application (app) interface as a graphical user interface or other user interface on the appointment scheduling modules 102 for allowing the client to communicate with the appointment scheduling modules 102.

Furthermore, the system 100 comprises a non-transitory, computer-readable storage medium, for example, a memory unit 105, and at least one processor 107 communicatively coupled to the non-transitory, computer-readable storage medium. As used herein, "non-transitory computer-readable storage medium" refers to all computer-readable media that contain and store computer programs and data, except for a transitory, propagating signal. Examples of the computer-readable media comprise hard drives, solid state drives, optical discs or magnetic disks, memory chips, a read-only memory (ROM), a register memory, a processor cache, a random-access memory (RAM), etc. The non-transitory, computer-readable storage medium stores computer program instructions and data defined by the modules 102 and 104 and modules, for example, 106a, 106b, 106c, etc., of the appointment optimization and route planning system (AORPS) 106. In an embodiment, the AORPS 106 is installed and stored in the memory unit 105 of the computing platform 101. In an embodiment, the appointment scheduling modules 102 and the mapping module 104 are also installed and stored in the memory unit 105. The memory unit 105 is used for storing program instructions, applications, and data. The memory unit 105 comprises, for example, a random-access memory (RAM) or another type of dynamic storage device that stores information and instructions for execution by the processor 107. The memory unit 105 also stores temporary variables and other intermediate information used during execution of the instructions by the processor 107. The computing platform 101 further comprises a read only memory (ROM) or another type of static storage device that stores static information and instructions for execution by the processor 107. In an embodiment, the memory unit 105 stores the logic of the appointment scheduling modules 102, the mapping module 104, and the modules, for example, 106a, 106b, 106c, etc., of the AORPS 106. The processor 107 executes the logic and renders data, travel routes, and appointment schedules to web and mobile apps executable on client devices and other user devices using application programming interfaces (APIs).

The processor 107 executes the computer program instructions defined by the appointment scheduling modules 102, the mapping module 104, and the modules, for example, 106a, 106b, 106c, etc., of the appointment optimization and route planning system (AORPS) 106. The processor 107 refers to any of one or more microprocessors, central processing unit (CPU) devices, finite state machines, computers, microcontrollers, digital signal processors, logic, a logic device, a user circuit, an application specific integrated circuit (ASIC), a field-programmable gate array (FPGA), a chip, etc., or any combination thereof, capable of executing computer programs or a series of commands, instructions, or state transitions. In an embodiment, the processor 107 is implemented as a processor set comprising, for example, a programmed microprocessor and a math or graphics co-processor. The processor 107 is selected, for example, from the Intel® processors such as the Itanium® microprocessor or the Pentium® processors, Advanced Micro Devices (AMD®) processors such as the Athlon® processor, UltraSPARC® processors, microSPARC® processors, hp® processors, International Business Machines (IBM®) processors such as the PowerPC® microprocessor, the MIPS® reduced instruction set computer (RISC) processor of MIPS Technologies, Inc., RISC based computer processors of ARM Holdings, Motorola® processors, Qualcomm® processors, etc. The AORPS 106 disclosed herein is not limited to employing a processor 107. In an embodiment, the AORPS 106 employs a controller or a microcontroller.

As exemplarily illustrated in FIG. 1, the system 100 further comprises a radio frequency (RF) unit 109, a network interface 110, an input/output (I/O) controller 111, input devices 112, a fixed media drive 113 such as a hard drive, a removable media drive 114 for receiving removable media, output devices 115, a data bus 116, an antenna 117, and a display screen 108, on which, a graphical user interface (GUI) 108a is displayed for interaction with a user via the computing platform 101. The data bus 116 permits communications between the components, for example, 103, 105, 107, 108, 109, 110, 111, 112, 113, 114, 115, etc., of the appointment optimization and route planning system (AORPS) 106. The RF unit 109 allows transmission and/or reception of radio signals between the computing platform 101 and other computing devices, for example, the client device 119, electronic devices used by the patients, the healthcare providers, and the onsite care coordinators, etc., via the antenna 117. The display screen 108 comprises, for example, a video display, a liquid crystal display, a plasma display, an organic light emitting diode (OLED)-based display, etc. The GUI 108a is, for example, an online web interface, a web-based downloadable application interface, a mobile-based downloadable application interface, etc.

The network interface 110 enables connection of the appointment optimization and route planning system (AORPS) 106 in the computing platform 101 to the network 118. In an embodiment, the network interface 110 is provided as an interface card also referred to as a line card. The network interface 110 comprises, for example, of an infrared (IR) interface, an interface implementing Wi-Fi® of Wi-Fi Alliance Corporation, a universal serial bus (USB) interface, a FireWire® interface of Apple Inc., an Ethernet interface, a frame relay interface, a cable interface, a digital subscriber line (DSL) interface, a token ring interface, a peripheral controller interconnect (PCI) interface, a local area network (LAN) interface, a wide area network (WAN) interface, interfaces using serial protocols, interfaces using parallel protocols, Ethernet communication interfaces, asynchronous transfer mode (ATM) interfaces, a high speed serial interface (HSSI), a fiber distributed data interface (FDDI), interfaces based on a transmission control protocol (TCP)/internet protocol (IP), interfaces based on wireless communications technology such as satellite technology, RF technology, near field communication (NFC), etc. The I/O controller 111 controls input actions and output actions performed by the AORPS 106.

The input devices 112 of the computing platform 101 are used for inputting data into the appointment optimization and route planning system (AORPS) 106. A user of the computing platform 101 uses the input devices 112 to input data, for example, patient data, client data, and other data including training data for generating a predictive model and any updates to algorithms used in the AORPS 106. The input devices 112 are, for example, a keyboard such as an alphanumeric keyboard, a microphone, a joystick, a pointing device such as a computer mouse, a touch pad, a light pen, a physical button, a touch sensitive display device, a track ball, a pointing stick, any device capable of sensing a tactile input, etc.

In an embodiment as exemplarily illustrated in FIG. 1, the appointment optimization and route planning system (AORPS) 106 comprises a data reception module 106a, an input processing module 106b, an output generation module 106c, and one or more databases 106d stored in the memory unit 105. The database(s) 106d of the AORPS 106 is any storage area or medium used for storing data and files. In an embodiment, the database(s) 106d is, for example, any of a structured query language (SQL) data store or a not only SQL (NoSQL) data store such as the Microsoft® SQL Server®, the Oracle® servers, the MySQL® database of MySQL AB Limited Company, the mongoDB® of MongoDB, Inc., the Neo4j graph database of Neo Technology Corporation, the Cassandra database of the Apache Software Foundation, the HBase® database of the Apache Software Foundation, etc. In another embodiment, the database(s) 106d is a location on a file system. In another embodiment, the database(s) 106d is remotely accessible by the AORPS 106 via the network 118. In another embodiment, the database(s) 106d is configured as a cloud-based database implemented in a cloud computing environment, where computing resources are delivered as a service over the network 118. As used herein, "cloud computing environment" refers to a processing environment comprising configurable, computing, physical, and logical resources, for example, networks, servers, storage media, virtual machines, applications, services, etc., and data distributed over the network 118. The cloud computing environment provides on-demand network access to a shared pool of the configurable, computing, physical, and logical resources. In an embodiment, the AORPS 106 is a cloud computing-based platform implemented as a service for optimizing home-visit appointments and related travel for delivering patient care. In various embodiments, the AORPS 106 is developed, for example, using the Google App engine cloud infrastructure of Google Inc., Amazon Web Services® of Amazon Technologies, Inc., the Amazon elastic compute cloud EC2® web service of Amazon Technologies, Inc., the Google® Cloud platform of Google Inc., the Microsoft® Cloud platform of Microsoft Corporation, etc.

The appointment optimization and route planning system (AORPS) 106 optimizes home-visit appointments and related travel for delivering patient care using algorithms comprising, for example, one or more of decision trees, machine learning (ML) models, and regression models in the modules 106a, 106b, and 106c. The data reception module 106a receives registration data and patient data from patients. Moreover, the data reception module 106a receives client input from a client, for example, an administrator of a healthcare company that coordinates with healthcare providers and onsite care coordinators for scheduling the home-visit appointments. The client input comprises, for example, hours of availability of healthcare providers and onsite care coordinators, appointment types, health plan commitments, and a success rate of operation. The data reception module 106a receives the registration data and the patient data from the patients and the client input from the client through the appointment scheduling modules 102 via the network 118. In an embodiment, the data reception module 106a provides a web interface or a mobile application (app) interface as a graphical user interface (GUI) or another interactive user interface on the appointment scheduling modules 102 for the patients and the client to input data depending on the electronic device used by the patients and the client to communicate with the appointment scheduling modules 102 via the network 118. The client has the option of using the client device 119 for communicating with the appointment scheduling modules 102, where the client device 119 is dedicated for use in healthcare and comprises the GUI or another interactive user interface provided by the data reception module 106a preinstalled thereon. Furthermore, the data reception module 106a receives feedback from the patients, the client, the healthcare providers, and the onsite care coordinators after home-visit appointments. The data reception module 106a receives the feedback through the web or the mobile app interface on the appointment scheduling modules 102 via the network 118.

The registration data comprises identification information used for creating an account for the patient, that is secured, for example, with one or more of a password, a passkey, a hardware key, two-factor authentication, phone authentication through messaging or phone calls with one-time passcodes, etc., and with options for the patient to choose from an array of security features. For example, the registration data comprises an email address and/or a phone number of the patient or a representative of the patient and an acceptably secure password chosen by the patient or the representative of the patient. The patient data of each patient comprises, for example, age, gender, location of residence, profession, health information including height, weight, blood type, allergies and conditions, a list of chronic conditions, healthcare programs enrolled by the patient such as urgent care on demand, a primary care provider (PCP) program, and/or a chronic care management (CCM) program, a free-form self-report about current health, feeling, etc., reasons to get medical care if needed, clinical notes, any lab test results and other medical history, emergency contact information of trusted contacts or family members, preferred time bounds to interact with onsite care coordinators and/or healthcare providers, and payment information or payment methods. The data reception module 106a provides the web interface or the mobile app interface on the appointment scheduling modules 102 as a computer-aided interface with algorithms to match user-provided data with standard ontologies of health-related information in real time and to provide input suggestions for symptoms, conditions, drug names, etc., to the patients while the patients input the patient data.

For collecting the patient data, the data reception module 106a derives age from the date of birth of the patient or from a direct specification of the age made by the patient when the date of birth is not known. The data reception module 106a allows the patient to select a profession of the patient from a predefined list or to specify the profession in free-form text. The data reception module 106a allows the patient to select chronic conditions from a list or to type the chronic conditions as free-form text. In an embodiment, the list rendered by the data reception module 106a to select the chronic conditions is based on the $10^{th}$ revision of the International Statistical Classification of Diseases and Related Health Problems (ICD-10). Self-report is free-form text where a patient describes his or her feeling and health problems or concerns. The data reception module 106a also allows the patient to provide any health-related materials such as clinical notes from previous doctor visits in the form of text, lab test results in the form of text and as a table, etc. The data reception module 106a allows the patient to specify location, for example, as text, or by obtaining the location from geo-position facilities of the patient's device. The data reception module 106a allows the patient to specify a preferred time to meet onsite care coordinators and/or healthcare providers in different levels of detail, for example, time of day, day(s) of the week, and in more complex patterns. The data reception module 106a uses natural language processing (NLP) tools to process patient self-reports, clinical notes, lab test results, etc., to obtain data about conditions a patient has at the present and had in the past, results of lab tests, medication taken by the patient, etc. The data reception module 106a maps the patient data as the patient data is being received from patients to custom ontologies, for example, based on the Systematized Nomenclature of Medicine (SNOMED), the RxNorm® normalized naming system for generic and branded drugs, and Logical Observation Identifiers Names and Codes (LOINC).

The client input that the data reception module 106a receives from the client comprises, for example, information about healthcare providers, onsite care coordinators, appointment types, health plan commitments, and a success rate of operation. The success rate of operation refers to the rate of successful fulfillment of appointments scheduled for home visits. The client input further comprises, for example, dates and times of availability of the healthcare providers and the onsite care coordinators over a preconfigured period of time, for example, the next thirty days. The appointment scheduling modules 102 are also accessible to the healthcare providers and the onsite care coordinators via the network 118 for providing inputs about dates and times of their availability. Therefore, the data reception module 106a is able to receive the availability of the healthcare providers and the onsite care coordinators directly from them, thereby obviating the need for the client to communicate with the healthcare providers and the onsite care coordinators to obtain their availability to provide corresponding inputs to the data reception module 106a. As part of the health plan commitments, the client input comprises, for example, a list of patients from healthcare plans of the client and patients referred by primary care providers (PCP) attached to the healthcare plans. The appointment types comprise, for example, appointments with only the healthcare providers remotely available, appointments with only the onsite care coordinators remotely available, appointments with only the onsite care coordinators visiting onsite, and appointments with the healthcare providers remotely available and the onsite care coordinators visiting onsite.

The input processing module 106b collates the patient data received by the data reception module 106a. In collating the patient data, the input processing module 106b captures and organizes information about physical addresses of the patients, comorbidities, chronic conditions, current state of health of each patient, lab test results with dates of the same, prescribed medication and adherence of each patient to their prescriptions, time of last visit to a doctor for each patient, social and/or psychosocial determinants of health, religious beliefs, family status, gender, community to which the patient belongs, outstanding traits, insurance plans, insurance plan needs, and other relevant data in accordance with standard ontologies of health-related information. Furthermore, the input processing module 106b generates an input matrix based on the client input and the collated patient data, covering a preconfigured period of time, for example, thirty days. The input matrix comprises schedules of the healthcare providers and the onsite care coordinators, patient cohorts, expected minimum daily and maximum monthly volumes of appointments, and success rates of the appointments.

In an embodiment, the output generation module 106c is an artificial intelligence (AI)-enabled module configured to execute AI algorithms for optimizing home-visit appointments and related travel for delivering patient care. The output generation module 106c generates a predictive model for home-visit appointments for the patients, capitation for the healthcare providers and the onsite care coordinators, and return on investment (ROI) for all stakeholders for delivering patient care, based on training data comprising appointment and patient history, feedback, and healthcare data. The output generation module 106c uses feedback that the data reception module 106a receives from the patients, the client, the healthcare providers, and the onsite care coordinators during and after home-visit appointments, for generating the predictive model. The healthcare data in the training data comprises, for example, healthcare information of cohorts similar to the patients in terms of demographics and comorbidities, costs of healthcare implementations in a country, and insurance information. The output generation module 106c obtains information about the cohort of patients registered by the data reception module 106a from the patient data collated by the input processing module 106b. In an embodiment, the output generation module 106c obtains healthcare information comprising, for example, healthcare statistics, demography, information on cohorts of patients with specific conditions and comorbidities, costs involved in healthcare implementations, available healthcare programs, and insurance information from the database(s) 106d, which contain data compiled from trusted and verified sources and constantly updated manually on the computing platform 101.

The output generation module 106c also obtains healthcare data from trusted sources 120 through the data reception module 106a via the network 118. The output generation module 106c obtains healthcare data, for example, electronic health records (EHR), vital records, health statistics, administrative data, claims data of insured patients, patient/disease registries such as those from the National Cardiovascular Data Registry (NCDR) and the Surveillance, Prevention, and Management of Diabetes Mellitus (SU-PREME DM) DataLink, health surveys such as the Medicare Current Beneficiary Survey and the National Health and Nutrition Examination Survey (NHANES), clinical trials data, peer-reviewed literature, etc. Through the data reception module 106a, the output generation module 106c communicates with trusted sources 120, for example, healthcare delivery systems, insurance companies including Medicare, the National Library of Medicine, the National Center for Health Statistics (NCHS), the U.S. Department of Health and Human Services, the U.S. Centers for Medicare and Medicaid Services, and the Centers for Disease Control and Prevention through their outreach programs. The output generation module 106c compares the information about the cohort of patients registered in the system 100 with relevant healthcare information in the country to derive the healthcare data in the training data.

The output generation module 106c generates an appointment schedule with travel routes via the mapping module 104 using the global navigation satellite system (GNSS) module 103. The output generation module 106c generates the appointment schedule considering the physical locations of the patients obtained from the collated patient data as one of the factors among other optimization factors. The output generation module 106c uses the physical addresses of the patients corresponding to each appointment that involves onsite visits by the onsite care coordinators to have travel routes mapped out optimally by the mapping module 104, ensuring greatest possible coverage of patients given the availability and locations of the onsite care coordinators. The mapping module 104 communicates with the GNSS module 103, for example, a global positioning system (GPS) unit, to map out the travel routes as determined by the output generation module 106c. The output generation module 106c generates the appointment schedule with the travel routes dynamically based on optimization factors derived from the received client input, the collated patient data, the generated input matrix, the healthcare data, and the generated predictive model. The output generation module 106c generates the appointment schedule with the travel routes dynamically by incorporating real-time changes in the patient data, the client input, the optimization factors, and appointments. The output generation module 106c also optimizes the number of visits per month for each of the patients based on the optimization factors in the generation of the appointment schedule. In an embodiment, the output generation module 106c utilizes one or more of decision trees, machine learning models, and regression models for generating and executing the predictive model and for generating the appointment schedule.

The optimization factors comprise multiple criteria, one of which is patient care needs. Patient care needs comprise, for example, comorbidities, specific chronic conditions that are gleaned from either electronic medical records (EMR) or patient intake forms that are part of the patient data, insurance plan requirements and guidelines, suggested cadence or visit pattern of appointments, equipment required in patient care for each patient, and knowledge of any healthcare programs in which a patient is enrolled, for example, urgent care on demand, continuum of care based on a primary care provider (PCP) mode, and/or continuum of care based on chronic care management (CCM) programs. The optimization factors further comprise, for example, addresses of the patients, social and/or psychosocial determinants of health of the patients for clustering patients with similar determinants, religious beliefs, family status, gender, community to which a patient belongs, and outstanding traits for matching appropriate healthcare providers and onsite care coordinators to each patient. Furthermore, the optimization factors comprise, for example, information on insurance plans and insurance plan needs for clustering patients similar in that regard, availability of the healthcare providers and the onsite care coordinators, driving distances to the locations of the patients to minimize driving, and acceptance and rejections of scheduled appointments by the patients for rescheduling appointments that are rejected by the patients. Furthermore, the optimization factors comprise, for example, an appointment cancellation probability for each patient based on historical data about visit cancellation or absence in the past and patient data such as age, gender, social status, etc. The algorithms, including machine learning algorithms, underlying the output generation module 106c do not receive any information in the training data that cast patients into stereotypes or otherwise induce frivolous decisions when calculating the appointment cancellation probabilities. The output generation module 106c takes into account practical considerations, for example, medical issues with memory retention, prior history both with the system 100 and outside as gleaned from EMRs, and free-form self reports submitted by the patients themselves.

The output generation module 106c makes the generated appointment schedule with the travel routes available to the appointment scheduling modules 102. Through the appointment scheduling modules 102, the output generation module 106c conveys the generated appointment schedule with the travel routes to the concerned patients ensuring each patient receives only details of their appointment, the client, the healthcare coordinators, and the onsite care coordinators via the network 118 through notifications and updates on electronic devices used by the stakeholders and on the client device 119. The appointment scheduling modules 102 convey the generated appointment schedule with the travel routes to the client and only relevant appointment information from the appointment schedule to corresponding patients. In an embodiment, the output generation module 106c, via the appointment scheduling modules 102, communicates real-time updates comprising live tracking of the onsite care coordinators en route to home-visit appointments on a map to electronic devices of the patients, the onsite care coordinators, and the healthcare providers and to the client device 119 of the client involved in the concerned home-visit appointment starting from a predetermined time, for example, thirty minutes before the scheduled home-visit appointments. The client device 119 comprises hardware specific to the requirements of healthcare, for example, surviving drops, spills, and disinfection with strong chemicals, viewing and editing patient forms and reports including images in high resolution, viewing real-time graphs of vital signs, dedicated buttons for one-touch calls to healthcare providers and emergency services and for cost calculations, replaceable batteries. Moreover, the client device 119 comprises hardware and software tailored to the specific communication requirements between the client and the appointment scheduling modules 102, for example, for sending the client input and feedback about home-visit appointments. The client device 119 further comprises features for data acquisition, security, and robust communication, both wireless and wired. Patient care comprising, for example, diagnostics, medical procedures, and prescriptions in the home-visit appointments are carried out by the onsite care coordinators and/or the healthcare providers based on a mode of appointment through prevailing telemedicine practices. Medical kits and diagnostic equipment that the onsite care coordinators use at the patient's location during a home-visit appointment and that are suited for use with the appointment optimization and route planning system (AORPS) 106 and with telemedicine in general find examples in the Applicant's non-provisional patent application titled "Medical Diagnostic Kit", U.S. application Ser. No. 17/542,317, filed on Dec. 3, 2021, and in the Applicant's non-provisional patent application titled "Multi-organ Imaging System with a Single, Integrated Multi-Examination Illumination Unit", U.S. application Ser. No. 17/541,253, filed on Dec. 3, 2021.

The output generation module 106c assigns a mode of appointment to each home-visit appointment in the generated appointment schedule based on the optimization factors. The mode of appointment is based on the patient care needs, which is one of the criteria in the optimization factors. The output generation module 106c assigns a remote high-touch patient examination mode to those home-visit appointments where vital signs need to be monitored and involved diagnostics and medical procedures need to be done with a healthcare provider in attendance. In home-visit appointments with a remote, high-touch patient examination mode, the feedback that the data reception module 106a receives comprises data transmitted in real time during the home-visit appointment that the data reception module 106a then passes to the output generation module 106c. In such a home-visit appointment, healthcare providers situated at their offices remotely view data from a patient's location in real time through a telehealth bridge to a telehealth kit that onsite care coordinators use at the patient's location. For home-visit appointments such as follow-ups, prescription refills, and routine check-ins, where real-time data is not necessary, the output generation module 106c assigns a telehealth mode. Chronic care management (CCM) programs, for example, comprise a mix of the remote, high-touch patient examination mode and the telehealth mode that work together to utilize and optimize available resources based on a patients' needs.

The data reception module 106a receives any changes in the patient data and the client input, and responses and requests pertaining to the appointments from the client and the patients through the appointment scheduling modules 102 and passes on the same to the output generation module 106c. The communication between the appointment scheduling modules 102 and the patients, the client, the healthcare providers, and the onsite care coordinators occurs by means of the web or the mobile app interface on the appointment scheduling modules 102. The output generation module 106c dynamically adjusts the generated appointment schedule with the travel routes in real time based on changes in the optimization factors, changes in the patients, changes in the healthcare providers and the onsite care coordinators, and rejection of the appointments by the patients with minimal disruption.

Communication of the patients, the healthcare providers, the onsite coordinators, and the client with the modules 106a, 106b, and 106c of the appointment optimization and route planning system (AORPS) 106 is performed through the appointment scheduling modules 102. In an embodiment, the data reception module 106a receives the feedback including real-time patient care data during home-visit appointments with a remote high-touch patient examination mode, and changes, responses, and requests corresponding to the patient data, the client input, and the scheduled appointments from the patients, the client, the healthcare providers, and the on-site care coordinators through the appointment scheduling modules 102. The output generation module 106c makes available the generated appointment schedule with the travel routes and relevant real-time changes and updates to the appointment schedule and the travel routes including real-time tracking of on-site care coordinators' locations on a map to the appointment scheduling modules 102 that convey the same to the corresponding patients, the client, the healthcare providers, and the on-site care coordinators associated with and permitted to receive the corresponding information. The data reception module 106a receives the relevant permissions for access to personal and location information as part of the patient data and the client input from the patients and the client, the healthcare providers, and the on-site care coordinators respectively. For all this communication between the AORPS 106 and the patients, the client, the healthcare providers, and the on-site care coordinators, the data reception module 106a provides a web interface and a mobile app interface, comprising one or more application programming interfaces (API), on the appointment scheduling modules 102. When electronic devices or the client device 119 access the appointment scheduling modules 102 through the World Wide Web, they display and interact with the web interface, and when the devices access the appointment scheduling modules 102 through a mobile app designed for communication with the AORPS 106, they display and interact with the mobile app interface. Both the web interface and the mobile app interface provide the same information and experience to users differing only in underlying communication, abstracted from users, due to access from either the World Wide Web or a native mobile application on their electronic devices.

In an embodiment, the data reception module 106a of the AORPS 106 is communicated with directly through the input devices 112 and the output devices 115 in the computing platform 101 and/or via the network 118 when algorithms of the AORPS 106 are updated or when the output generation module 106c accesses healthcare information from the trusted sources 120 through the data reception module 106a directly via the network 118.

The output generation module 106c composes prompts and questions that are appropriate to a context of each home-visit appointment and makes the composed prompts and questions available to the appointment scheduling modules 102 accessed by the patients, the healthcare providers, and the onsite care coordinators through the web and/or the mobile app interface on the appointment scheduling modules 102. The data reception module 106a receives feedback to the prompts and the questions and free-form feedback from the patients, the healthcare providers, and the onsite care coordinators after the home-visit appointments. The output generation module 106c uses this feedback along with medical records of the patients, appointment and patient history, and healthcare data as training data for model training to subsequently generate the predictive model. In the initial stages for a new patient, when no feedback or appointment history is available yet, the feedback portion of the training data will not be available and the model training is performed based on the patient history obtained from the collated patient data and based on the client input and the healthcare data. In an embodiment, the output generation module 106c also obtains the healthcare data from the database(s) 106d or from the trusted sources 120 through the data reception module 106a. The output generation module 106c generates the predictive model by analyzing the training data using algorithms comprising, for example, decision trees, machine learning, and regression models. The output generation module 106c also executes artificial intelligence algorithms for generating and updating the predictive model in an agile environment.

In an embodiment, the training data for the generation of the predictive model and the optimization factors for the generation of the appointment schedule with the travel routes comprise, among other data, historical data. The historical data comprises, for example, feedback from the patients, the healthcare providers, the onsite care coordinators, and the client about fulfilled home-visit appointments, and data about acceptance or rejection of scheduled appointments, visit cancellation, absence for a scheduled home visit, changes in appointments or patient data by the patients, etc. Where such requisite prior data is not available, the output generation module 106c uses the collated patient data and the client input that the data reception module 106a receives and the healthcare information that the output generation module 106c accesses from the database(s) 106d and/or directly from the trusted sources 120 via the network 118 to the extent that they serve as useful input. As appointments are scheduled and fulfilled, the output generation module 106c obtains historical data from collected feedback and appointment history and uses the historical data as part of the training data to generate the predictive model and as part of the optimization factors to generate the appointment schedule with the travel routes accordingly.

The predictive model that the output generation module 106c generates analyzes the history of home-visit appointments by the healthcare providers and occupational healthcare consultants and the history of hospital and emergency room (ER) visits by the patients. Moreover, the predictive model performs competitive analysis against cohorts of patients, including cohorts not in the system 100, that are similar in terms of demographics and comorbidities by acquiring information about patients and healthcare from the trusted sources 120 through the data reception module 106a. Furthermore, the predictive model computes global savings from implementing healthcare programs, for example, urgent care, the primary care provider (PCP) program, the chronic care management (CCM) programs, etc. The predictive model also computes return on investment (ROI) for insurance plans and capitation projections for the insurance plans, the healthcare providers, and the onsite care coordinators. Furthermore, the predictive model predicts patient behaviors at various stages of the patient care process, including, for example, calculating appointment cancellation probabilities for the patients, and predicts potential outcomes and impacts of cohort analysis on capitation models. Therefore, the predictive model that the output generation module 106c generates comprises, for example, predicted patient behaviors, suggested cadence of appointments for each of the patients, predicted equipment requirements, appointment cancellation probabilities for each of the patients, potential outcomes, expected costs, capitation projections for insurance plans, and ROI for the insurance plans. Furthermore, the predictive model forms clusters of patients based on the collated patient data, the client input, the feedback in the training data, social and psychosocial determinants of health of the patients, insurance plans of the patients, and insurance plan needs of the patients.

Furthermore, in communication with the data reception module 106a, which provides a computer-aided web or mobile application interface to a patient while receiving patient data to match the data with standard ontologies in healthcare, the predictive model predicts related and possible health issues a patient may have based on the inputs of the patient in the patient data and the corresponding matches with standard ontologies that the data reception module 106a makes. Based on the patient data and the corresponding matches with the standard ontologies, the predictive model also predicts patient needs in terms of appointment type comfortable with and equipment required for the patient during a home-visit, for example, blood pressure measurement tools, electrocardiogram (ECG) tools, etc.

In an embodiment, the output generation module 106c computes a visit priority for each patient considering factors comprising, for example, patient needs and an appointment acceptance probability for each patient. The output generation module 106c calculates visit priorities based on a risk of an acute episode for a given patient. The output generation module 106c gauges the chances of an acute risk using information about a patient such as chronic conditions, current state of health, lab test results including how old the lab results are, prescribed drugs and how the patient follows prescriptions, and time of the last doctor visit. In the case of absence of time data, the worst case is assumed, for example, that a doctor was last seen more than a year ago, lab tests have expired, etc. The output generation module 106c uses the predictive model, trained on open-source and custom collected data, for a risk prediction. The output generation module 106c predicts risk in the form of a function describing acute episode probability that varies with time. Along with an appointment acceptance probability for each patient, the output generation module 106c also computes a rejection probability for each patient using historical data about visit cancellation and/or absence in the past. The output generation module 106c uses both state-of-the-art and custom algorithms and approaches to obtain visit cancellation probabilities based on patient data such as age, gender, social status, etc.

In the generation of the appointment schedule with the travel routes, the output generation module 106c executes algorithms that perform multiple steps of computing multiple parameters that take into account all the optimization factors. An exemplary sequence of steps is as follows. At first, the output generation module 106c populates a list of constraints that constitute requirements of the appointment schedule as exemplarily disclosed below:

(a) One requirement is that the appointment schedule should match a visit pattern of the patient. This pattern depends on patient conditions and history. For example, after a cardiovascular attack, a patient should be checked every week and, after a while, every month. Another example is that of an initial health check that is performed right after the patient registers with the system 100.

(b) Another requirement is that a home visit to a patient with a high appointment cancellation probability should be planned with some delay to give the patient time to respond and prepare for the home visit. This rule does not work for patients with high acute state risk and/or for the first visit after registration of a patient.

(c) Another requirement is that an appointment type and a list of equipment should match recommendations for a particular patient.

(d) Another requirement is that a home visit to a patient with a high acute state risk should be scheduled as early as possible.

(e) Another requirement is that the time of a home visit should match availability preferences of the patient, the onsite care coordinators, and/or the healthcare provider involved in the home visit.

(f) Yet another requirement is that time to perform all home visits for a single day by a particular onsite care coordinator and/or healthcare provider, including traveling time to the first home visit and back from the last home visit, should not exceed a working day.

After building the list of constraints, the output generation module 106c manifests optimization goals through a function to optimize. These goals are, for example, home visits with higher priority should happen earlier; and total time to perform all home visits should be as small as possible. To obtain an optimal solution matching described constraints, the output generation module 106c builds a mixed-integer programming (MIP) problem. The output generation module 106c uses a set of variables to indicate paths of travel of onsite care coordinators, presence of healthcare providers, and other parameters. The output generation module 106c manifests constraints through linear equalities and inequalities. The function for optimization is then a sum of home visit times weighted by visit priorities. The output generation module 106c solves the MIP problem built above using both standard and custom algorithms comprising, for example, branch-and-cut, genetic, heuristic, and other algorithms. The output generation module 106c calculates an optimal home-visit plan through a month starting from the current date. To ensure periodic schedule recalculation to match changes, the output generation module 106c recalculates the home-visit plan every day to follow changes in patient needs and healthcare provider and onsite care coordinator availability.

After solving the appointment scheduling problem, the output generation module 106c, in communication with the appointment scheduling modules 102 and the data reception module 106a, uses algorithms to coordinate and respond to interactions among the system 100, the patients, the client, the healthcare coordinators, and the onsite care coordinators. An exemplary sequence of steps is as follows:

(a) To inform the patients, the healthcare providers, and the onsite care coordinators about a recommended home-visit schedule, the output generation module 106c, via the appointment scheduling modules 102, sends the generated appointment schedule to the healthcare providers and the onsite care coordinators. At the same time, the appointment scheduling modules 102 send invitations for home-visit appointments to the patients.

(b) The healthcare providers and the onsite care coordinators view bookings as soon as the appointment scheduling modules 102 publish the appointment schedule via a web or a mobile application interface that the data reception module 106a provides on the appointment scheduling modules 102. The appointment scheduling modules 102 allow the healthcare providers and the onsite care coordinators to accept any home-visit that is suggested in the appointment schedule and confirmed by the corresponding patient. The output generation module 106c is configured to invalidate a booking if the corresponding patient does not accept the booking, for example, at least two hours in advance of the start of the appointment. The output generation module 106c reschedules unaccepted appointments in the next computation cycle.

(c) To dynamically update the appointment schedule according to feedback from the patients, the healthcare providers, and the onsite care coordinators, the output generation module 106c updates the appointment schedule with patient responses to invitations. If a particular patient confirms his or her appointment, the output generation module 106c fixes the appointment during all appointment schedule updates. If a patient rejects an invitation, the output generation module 106c removes the corresponding appointment for the home visit from further updates to the appointment schedule.

(d) If the data reception module 106a, via the appointment scheduling modules 102, does not receive a response to an invitation from the corresponding patient, the output generation module 106c, via the appointment scheduling modules 102, resends the invitation periodically. The output generation module 106c decreases the corresponding visit priority for the home-visit appointment each time the patient does not respond to the invitation. The output generation module 106c repeats this cycle until a predetermined threshold time before a home visit. The predetermined threshold time depends on, for example, the appointment type, number of participants, and other factors. If the data reception module 106a does not receive a response from the patient before the threshold time, the output generation module 106c cancels the home-visit appointment. In an embodiment, the output generation module 106c sends details of the cancelled home-visit appointment to the client's resources to schedule the home visit manually.

The output generation module 106c computes return on investment (ROI) by comparing the cohort of patients using the appointment optimization and route planning system (AORPS) 106 with a few slices of similar cohorts with both similar and different health plans, and clustering patients, for example, by similar age, conditions, and other social determinants of health. The output generation module 106c generates the appointment schedule according to risk in an attempt to cover home-visits to the most critical patients first, reducing unnecessary burden on the health system. A pseudocode illustrating calculations for computing the ROI for an exemplary scenario and an example of a corresponding table that results on execution of the pseudocode are disclosed below.

```
//medicare plan members
plan_members=50000
//total number of chronic conditions patients
ccm_total=0.03*n_members
//chronic care management (CCM) members hospitalized
   once a year
hsp_once=0.10*ccm_total
//CCM members hospitalized twice a year
hsp_twice=0.05*ccm_total
//CCM members hospitalized quarterly
hsp_qtr=0.02*ccm_total
//CCM members who had hospital readmissions after the
   initial admission
hsp_readm=0.20*(hsp_once+2*hsp_twice+4*hsp_qtr)
```

```
//CCM members who go into emergency room (ER) once
    a year
er_once=0.05*ccm_total
//CCM members who go into ER twice a year
er_twice=0.10*ccm_total
//CCM members who go into ER twice a year
er_qtr=0.15*ccm_total
//average cost of hospitalization for CCM patients
cost_hsp=12000
//average cost of hospital readmission for CCM patients
cost_readm=15200
//average cost of ER visit
cost_er=1500
//Probability of a CCM patient NOT getting into the
    Hospital or ER after a home-visit appointment
//Computed as Σ (FOREACH Specialty of Individual
    Probability of NOT getting into
ER/Hospital after home-visit for all patients with certain
    condition (i) times number of patients with such con-
    dition (i)) divided by the total members
//The Probability of NOT getting into ER/Hospital after a
    home-visit is based on an artificial intelligence (AI)
    model
hsp_er_proba_total=sum((FOREACH
    hsp_er_proba_i*n_members_i) over conditions (i))/
    n_members
//Total cost of hospitalization for CCM members of the
    plan
hsp_annual_cost=cost_hsp*(hsp_once+2*hsp_twice+
    4*hsp_qtr)*hsp_er_proba_total
//Total cost of hospital readmissions for CCM members of
    the plan
readm_annual_cost=cost_readm*hsp_readm*hsp_er_
    proba_total
//Total cost of ER visits for CCM members of the plan
er_annual_cost=cost_er*(er_once+2*er_twice+4*er_
    qtr)*hsp_er_proba_total
//Total cost for CCM members of the plan
total_annual_cost=hsp_annual_cost+readm_annual_
    cost+er_annual_cost
//Total savings for hospitalization for CCM members of
    the plan
zc_save_hsp=0.12*hsp_annual_cost
//Total savings for hospital readmissions for CCM mem-
    bers of the plan
zc_save_readm=0.15*readm_annual_cost
//Total savings for ER visits for CCM members of the plan
zc_save_er=0.25*er_annual_cost
//Total savings for CCM members of the plan
zc_save_total=zc_save_hsp+zc_save_readm+zc_save_er
//Total savings % for CCM members of the plan
zc_save_percent=zc_save_total/total_annual_cost
//Total number of CCM members NOT reached by the
    plan annually to come to the primary care provider
    (PCP)/routine appointment
ccm_unreachable=0.60*(hsp124+er_124)
//Total number of CCM members NOT reached by the
    plan that would agree to be visited via a home-visit
    appointment
ccm_unreach_served=0.50*ccm_unreachable
//Total $$ paid by the plan in a Per Member Per Month
    (PMPM) model if paid $10 per member
zc_save_pmpm=10*n_members
//Total $$ paid by the plan in a Fee For Service (FFS)
    model if paid $200 per encounter
zc_save_ffs=200*ccm_unreach_served
//margin for the hospital in PMPM model
zc_margin_pmpm=(zc_save_total-zc_save_pmpm)/
    zc_save_total
//margin for the hospital in FFS model
zc_margin_ffs=(zc_save_total-zc_save_ffs)/zc_save_to-
    tal
//revenues for the hospital in PMPM model
zc_revenue_pmpm=zc_save_pmpm+0.10*zc_save_total
//revenues for the hospital in FFS model
zc_revenue_ffs=200*ccm_unreach_served
```

| Assumptions | | Model | | |
|---|---|---|---|---|
| Plan Members | 50,000 | | | |
| % of CCM with complex problems | 30% | CCM | 15000 | |
| % of CCM in hospitals once a year | 10% | CCM in Hospital once a year | 1500 | |
| % of CCM in hospitals twice a year | 5% | CCM in Hospital twice a year | 750 | |
| % of CCM in hospitals quarterly | 2% | CCM in Hospital quarterly | 300 | |
| % of CCM in hospitals re-admissions | 20% | CCM in Hospital re-admissions | 840 | |
| % of CCM in ER once a year | 5% | CCM in ER once a year | 750 | |
| % of CCM in ER twice a year | 10% | CCM in ER twice a year | 1500 | |
| % of CCM in ER quarterly | 15% | CCM in ER quarterly | 2250 | |
| % of unreachable CCM in each category | 60% | Cost for Hospital admissions annual | $5,04,00,000.00 | * Risk Model |
| % of unreachable CCM served in each category | 50% | Cost for Hospital re-admissions annual | $1,27,68,000.00 | * Risk Model |

-continued

| Assumptions | | Model | | |
|---|---|---|---|---|
| % of people that will NOT get to ER/Hospital | RISK MODEL | Cost for ER visits annual | $1,91,25,000.00 | * Risk Model |
| | | Total plan costs | $8,22,93,000.00 | |
| Cost of Hospital admission | 12000 | | | |
| Cost of Hospital re-admission | 15200 | Savings for Hospital admissions annual | $ 60,48,000.00 | |
| Cost of ER visit | 1500 | Savings for Hospital re-admissions annual | $ 19,15,200.00 | |
| | | Savings for ER admissions annual | $ 47,81,250.00 | |
| | | Total savings | $1,27,44,450.00 | |
| Savings in Hospital admission | 12% | % of savings | 15.49% | |
| Savings in Hospital re-admission | 15% | | | |
| Savings in ER admission | 25% | Number of CCM members unreachable | 4230 | |
| | | Number of CCM members unreachable CCM served | 2115 | |
| Max Served per month | 5% | $25,000 Total Savings | $1,27,44,450.00 | |
| PMPM | $10 | Total Costs PMPM | $ 5,00,000.00 | |
| Per Visit | 200 | Total Costs FFS | $ 4,23,000.00 | |
| PMPM % Savings | 10% | Profit Margin PMPM | 96.08% | |
| | | Profit Margin FFS | 96.68% | |
| | | Revenues PMPM | $ 17,74,445.00 | |
| | | Revenues FFS | $ 4,23,000.00 | |

In an exemplary illustration, daily scheduling of appointments for onsite care coordinators and travel for the day performed by an embodiment of the appointment optimization and route planning system (AORPS) 106 follows the following steps. At the beginning of each working day, the output generation module 106c generates an appointment schedule for the onsite care coordinators for all home-visit appointments for the day. To generate the appointment schedule, the output generation module 106c considers all appointments including those requested by patients and those planned by the output generation module 106c for the day and confirmed by corresponding patients. The output generation module 106c then optimizes the appointments based on optimization factors to generate the appointment schedule. At first, the output generation module 106c adds two fake appointments with zero duration and with location as the office of the client availing the services of the AORPS 106 to represent the beginning, that is, the source of the working day, and the end, that is, the target of the working day. Next, the output generation module 106c creates an appointment graph according to a rule, for example: two appointments are adjacent to each other if the end time of the first appointment plus time to drive to the second appointment is less than the start time of the second appointment AND no more appointments could be served between these two appointments. Then, the output generation module 106c replaces all nodes of the appointment graph except the source node and the target node by a pair of nodes with a single edge between them. Next, the output generation module 106c defines a parameter, demand, and assigns the source node demand a number equal to (−1) times the number of onsite care coordinators (OCCs) and a target node demand a number equal to the number of onsite care coordinators. The output generation module 106c assigns capacity and weight parameters to the edges in the appointment graph. All edges get capacity 1 and weight −1. The output generation module 106c then executes a min-cost-max-flow algorithm to produce a flow between the source and the target. Every thread in this flow represents a route for a single onsite care coordinator. Unit-capacity edges, with a capacity 1, between split nodes guarantee that every node is visited once. A weight of −1 for all edges forces the algorithm to visit as many appointments as possible. During a day, the output generation module 106c executes the algorithm every time the list of appointments is changed. In this case, appointments already visited and completed are excluded. Furthermore, the algorithm takes into account any additional information by removing some edges. For example, if an onsite care coordinator reports a breakdown of a vehicle and a requirement of three hours to repair the vehicle, the algorithm removes all edges from the onsite care coordinator's current location to appointments before three hours from the present. Every hour, the output generation module 106c performs appointment bookings for appointments starting, for example, two to three hours from the present.

Along with hardware, computer applications and programs are used for operating the appointment optimization and route planning system (AORPS) 106 disclosed herein. The programs are loaded onto the fixed media drive 113 and into the memory unit 105 of the computing platform 101 via the removable media drive 114 exemplarily illustrated in FIG. 1. In an embodiment, the computer applications and programs are loaded directly on the computing platform 101 via the network 118. The output devices 115 of the computing platform 101 output the results of operations performed by the AORPS 106. For example, the AORPS 106 renders the GUI 108a for a user of the computing platform 101 to interact with the AORPS 106, using the output devices 115.

The processor 107 of the computing platform 101 exemplarily illustrated in FIG. 1, executes an operating system, for example, the Linux® operating system, the Unix® operating system, any version of the Microsoft® Windows® operating system, the Mac OS of Apple Inc., the IBM® OS/2, VxWorks® of Wind River Systems, Inc., QNX Neutrino® developed by QNX Software Systems Ltd., the Palm OS®, the Solaris operating system developed by Sun Microsystems, Inc., the Android® operating system of Google Inc., the Windows Phone® operating system of Microsoft Corporation, the BlackBerry® operating system of BlackBerry Limited, the iOS operating system of Apple Inc., the Symbian™ operating system of Symbian Foundation Limited, etc. The appointment optimization and route planning system (AORPS) 106 employs the operating system for performing multiple tasks. The operating system is responsible for management and coordination of activities and sharing of resources of the AORPS 106. The operating system further manages security of the AORPS 106, peripheral devices connected to the AORPS 106, and network connections. The operating system employed on the AORPS 106 recognizes, for example, inputs provided by a user of the AORPS 106 such as a user of the computing platform 101, using one of the input devices 112, the output devices 115, files, and directories stored locally on the fixed media drive 113. The operating system on the AORPS 106 executes different programs using the processor 107. The processor 107 and the operating system together define a computer for which application programs in high level programming languages are written. The operating system of the computing platform 101 determines the programming languages used in the AORPS 106. For example, the Java® programming language is used for developing the AORPS 106 on the computing platform 101 with an Android® operating system, while Objective-C® of Apple Inc., is used for developing the AORPS 106 on the computing platform 101 with the iOS operating system, and the UNITY® libraries and platforms of Unity IPR ApS, LLC., are used developing the AORPS 106 for both the Android® operating system and the iOS operating system.

The processor 107 retrieves instructions defined by the appointment scheduling modules 102 and the mapping module 104 stored in the memory unit 105, for performing respective functions disclosed above. The processor 107 also retrieves instructions defined by the data reception module 106a, the input processing module 106b, and the output generation module 106c of the appointment optimization and route planning system (AORPS) 106 stored in the memory unit 105, for performing respective functions disclosed above. The processor 107 retrieves the instructions for executing the modules 102 and 104 and the modules, for example, 106a, 106b, 106c, etc., of the AORPS 106 from the memory unit 105. A program counter determines the location of the instructions in the memory unit 105. The program counter stores a number that identifies the current position in a program of each of the modules 102 and 104 and each of the modules, for example, 106a, 106b, 106c, etc., of the AORPS 106. The instructions fetched by the processor 107 from the memory unit 105, after being processed, are decoded. The instructions are stored in an instruction register in the processor 107. After processing and decoding, the processor 107 executes the instructions, thereby performing processes defined by those instructions.

At the time of execution, the instructions stored in the instruction register are examined to determine the operations to be performed. The processor 107 then performs the specified operations. The operations comprise arithmetic operations and logic operations. The operating system performs multiple routines for performing a number of tasks required to assign the input devices 112, the output devices 115, and the memory unit 105 for execution of the modules 102 and 104 and the modules, for example, 106a, 106b, 106c, etc., of the appointment optimization and route planning system (AORPS) 106. The tasks performed by the operating system comprise, for example, assigning memory to the modules 102 and 104 and to the modules, for example, 106a, 106b, 106c, etc., of the AORPS 106, and to data used by the AORPS 106, moving data between the memory unit 105 and disk units, and handling input/output operations. The operating system performs the tasks on request by the operations, and after performing the tasks, the operating system transfers the execution control back to the processor 107. The processor 107 continues the execution to obtain outputs.

Figure 2A:
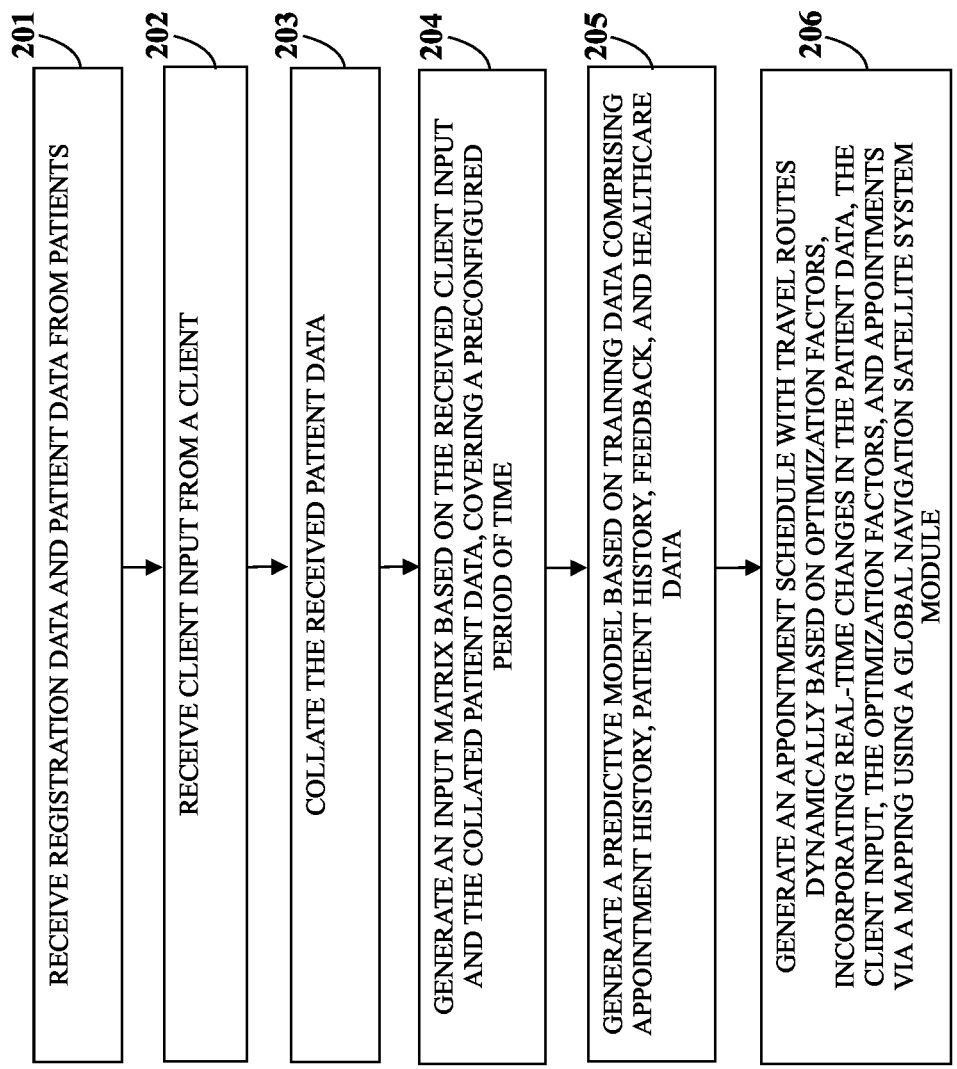
FIG. 2A illustrates a flowchart of an embodiment of a computer-implemented method for optimizing home-visit appointments and related travel for delivering patient care.

FIG. 2A illustrates a flowchart of an embodiment of a computer-implemented method for optimizing home-visit appointments and related travel for delivering patient care. The computer-implemented method disclosed herein employs the appointment optimization and route planning system (AORPS) 106 exemplarily illustrated in FIG. 1, that defines computer program instructions and data stored in a non-transitory, computer-readable storage medium. At least one processor 107 communicatively coupled to the non-transitory, computer-readable storage medium, for example, the memory unit 105 exemplarily illustrated in FIG. 1, executes the computer program instructions of the AORPS 106 for performing the method for optimizing home-visit appointments and related travel for delivering patient care. Moreover, the AORPS 106 communicates with one or more appointment scheduling modules 102, the global navigation satellite system (GNSS) module 103, and the mapping module 104 exemplarily illustrated in FIG. 1. The AORPS 106 communicates with a client, for example, an administrator in a healthcare company availing the services of the AORPS 106, patients using the AORPS 106 via the client, and healthcare providers and onsite care coordinators involved in delivering patient care to the patients through the appointment scheduling modules 102. The client coordinates with the healthcare providers and the onsite care coordinators for the home-visit appointments. The AORPS 106 provides a web interface or a mobile application (app) interface on the appointment scheduling modules 102 for the patients and the client to input data depending on the electronic devices used by the patients and the client to communicate with the appointment scheduling modules 102 via the network 118 exemplarily illustrated in FIG. 1. The AORPS 106 also communicates with the client via the client device 119 provided to the client for communicating with the appointment scheduling modules 102. The client device 119 is dedicated for use in healthcare and comprises a preinstalled, graphical user interface (GUI) or another interactive user interface provided by the AORPS 106. The AORPS 106 optimizes travel to locations of the patients for onsite appointments utilizing maps and live locational information, traffic conditions, weather conditions, etc., through the mapping module 104. The mapping module 104 is in operable communication with the GNSS module 103, for example, a global positioning system (GPS) unit. The functions and operations of the appointment scheduling modules 102, the GNSS module 103, the mapping module 104, and the client device 119 are disclosed in the description of FIG. 1.

In the computer-implemented method disclosed herein, the appointment optimization and route planning system (AORPS) 106 receives 201 registration data and patient data from patients. The registration data comprises information required of a patient to create an account on the AORPS 106. The patient subsequently communicates with the AORPS 106 through the account, thereby allowing the AORPS 106 to associate all communication and data exchanged with the patient with his or her account. The registration data comprises identification details, for example, an email address and/or a phone number of the patient or a representative of the patient. Moreover, the registration data comprises, for example, an alphanumeric password chosen by the patient or the representative of the patient that meets acceptable standards of security that the AORPS 106 conveys to the patient while receiving the registration data. In an embodiment, the AORPS 106 also accepts a passkey, two-factor authentication information using a software authenticator application or a hardware key, phone authentication through messaging or phone calls with one-time-passcodes, etc., instead of a password. The patient data comprises, for example, age, gender, profession, location, lists of chronic health conditions, medical history, healthcare programs enrolled by the patients, for example, urgent care on demand, a primary care provider (PCP) program, and/or a chronic care management (CCM) program, free-form self-reports about current health, reasons for requiring medical attention, clinical notes and other medical history, emergency contact information of trusted contacts, preferred time bounds to interact with healthcare providers and onsite care coordinators involved in patient care during home-visit appointments, and payment information. The AORPS 106 matches input from the patients, while receiving the patient data in real time, with standard ontologies of health-related information to provide input suggestions to the patients while receiving the patient data.

The appointment optimization and route planning system (AORPS) 106 receives 202 client input from the client to schedule home-visit appointments with healthcare providers and onsite care coordinators for the patients under its care. The client input comprises, for example, information about hours of availability of healthcare providers and onsite care coordinators, appointment types, health plan commitments, and a success rate of operation. The appointment types comprise, for example, four scenarios of appointments: appointments with only the healthcare providers remotely available, appointments with only the onsite care coordinators remotely available, appointments with only the onsite care coordinators visiting onsite, and appointments with the healthcare providers remotely available and with the onsite care coordinators visiting onsite. As part of the health plan commitments, the client input comprises a list of patients from healthcare plans of the client and patients referred by primary care providers (PCP) attached to the healthcare plans. The success rate of operation is the rate of successful fulfillment of appointments scheduled for home visits. The AORPS 106 collates 203 the received patient data to capture information about patients' addresses, comorbidities, chronic conditions, current state of health of each patient, lab test results with dates, prescribed medication and adherence of each patient to their prescriptions, and time of last visit to a doctor by each patient. In an embodiment, in collating the patient data, the AORPS 106 captures and organizes social and/or psychosocial determinants of health, religious beliefs, family status, gender, community to which each patient belongs, outstanding traits, insurance plans, insurance plan needs, and other relevant data for clustering similar patients and for matching appropriate healthcare providers and onsite care coordinators to each patient.

The appointment optimization and route planning system (AORPS) 106 generates 204 an input matrix based on the received client input and the collated patient data, covering a preconfigured period of time, for example, thirty days. The input matrix comprises schedules of the healthcare providers and the onsite care coordinators, patient cohorts, expected minimum daily and maximum monthly volumes of appointments, and success rates of the appointments. The AORPS 106 generates 205 a predictive model for appointments, capitation, and return on investment (ROI) for delivering patient care based on training data comprising appointment history, patient history, feedback, and healthcare data. The AORPS 106 receives feedback from the patients, the client, the healthcare providers, and the onsite care coordinators after home-visit appointments. This feedback is used as part of the training data for generating and updating the predictive model. For the first appointments where feedback is not yet available, the AORPS 106 trains the predictive model using patient history obtained from the collated patient data, the client input, and the healthcare data. The healthcare data comprises, for example, healthcare information of cohorts similar to the patients in terms of demographics and comorbidities, costs of healthcare implementations in a country, and insurance information that the AORPS 106 obtains from trusted sources 120 exemplarily illustrated in FIG. 1, and verified sources and that is maintained to be current with prevailing circumstances.

The appointment optimization and route planning system (AORPS) 106 generates 206 an appointment schedule with travel routes dynamically based on optimization factors derived from the received client input, the collated patient data, the generated input matrix, the healthcare data, and the generated predictive model. The optimization factors comprise, for example, patient care needs comprising comorbidities of the patients, specific chronic conditions derived from either electronic medical records (EMRs) or patient intake forms, insurance plan requirements and guidelines, suggested cadence, this is, visit pattern, of appointments, equipment required for each appointment, appointment cancellation probability of each patient based on historical data about visit cancellation or absence in the past, patient data such as age, gender, social status, etc., addresses of the patients, social and/or psychosocial determinants of health of the patients for clustering similar patients, religious beliefs, family status, gender, community to which each patient belongs, and outstanding traits for matching healthcare providers and onsite care coordinators to each patient, insurance plans and insurance plan needs for clustering similar patients, availability of the healthcare providers and the onsite care coordinators, minimization of driving for the home-visit appointments, and acceptance and rejections of scheduled appointments by the patients for rescheduling of the appointments in cases of rejection of the scheduled appointments.

In an embodiment, the appointment optimization and route planning system (AORPS) 106 assigns a mode of appointment to each appointment in the generated appointment schedule based on the patient care needs that are a part of the optimization factors. For home-visit appointments where live monitoring and transfer of real-time data is essential for healthcare providers to provide patient care with onsite care coordinators at the patients' locations, the AORPS 106 assigns a remote, high-touch patient examination mode. In a home-visit appointment with the remote, high-touch patient examination mode, healthcare providers, situated at their offices, remotely view data from a patient's location in real time through a telehealth bridge to a telehealth kit that onsite care coordinators use at the patient's location. For home-visit appointments where real-time data transmission is not essential, for example, for follow-ups, prescription refills, and routine check-ins, the AORPS 106 assigns a telehealth mode. Chronic care management (CCM) programs, for example, include a mix of the remote, high-touch patient examination mode and the telehealth mode that work together to utilize and optimize available resources based on a patients' needs.

The appointment optimization and route planning system (AORPS) 106 sends the generated appointment schedule with the travel routes to the client and relevant appointment information from the appointment schedule to corresponding patients. Furthermore, the AORPS 106 receives any changes in the patient data and the client input, and responses and requests pertaining to the appointments from the client and the patients. The AORPS 106 incorporates real-time changes in the patient data, the client input, the optimization factors, and the appointments via a mapping through the mapping module 104 and the GNSS module 103 that uses a global navigation satellite system, for example, a global positioning system (GPS) unit. In an embodiment, the AORPS 106 optimizes the appointment schedule with the travel routes in real time by dynamically adjusting the appointment schedule with the travel routes in real time based on changes in the optimization factors, changes in the patients, changes in the healthcare providers and the onsite care coordinators, and rejection of the appointments by the patients with minimal disruption. The AORPS 106 optimizes home-visit appointments and related travel for delivering patient care using algorithms comprising, for example, one or more of decision trees, machine learning models, and regression models. In an embodiment, the AORPS 106 performs the generation and execution of the predictive model and the generation of the appointment schedule utilizing one or more of decision trees, machine learning models, and regression models. After the home-visit appointments, the AORPS 106 receives feedback from the patients, the client, the healthcare providers, and the onsite care coordinators, for example, as both comments and responses to prompts and questions that the AORPS 106 poses. The AORPS 106 utilizes this feedback as part of the training data to generate and update the predictive model.

The predictive model that the appointment optimization and route planning system (AORPS) 106 generates comprises predicted patient behaviors, suggested cadence of appointments for each of the patients, predicted equipment requirements, appointment cancellation probabilities for each of the patients, potential outcomes, expected costs, capitation projections for insurance plans, return on investment (ROI) for the insurance plans, and clusters of patients based on the collated patient data, the client input, the feedback in the training data, social and psychosocial determinants of health of the patients, insurance plans of the patients, and insurance plan needs of the patients. In generating the predictive model, the AORPS 106 applies regression models, decision trees, machine learning, and artificial intelligence to glean insights into the vast amount of data collected by the AORPS 106 from all stakeholders comprising the patients, the client, the healthcare providers, and the onsite care coordinators at various stages of patient care from initial contact to post-appointment feedback and from trusted external sources as healthcare data. The AORPS 106 receives and organizes data on various aspects of healthcare and personality traits from multiple sources for clustering similar patients, for matching appropriate healthcare providers and onsite care coordinators to each patient, and for delivering appropriate, relevant, impactful, and personal patient care to each patient.

The appointment optimization and route planning system (AORPS) 106 executes algorithms comprising, for example, decision trees, machine learning, regression modeling, and artificial intelligence in collating the patient data, deciding on relevant healthcare data to be acquired from trusted sources 120, generating the input matrix, composing questions that are relevant and appropriate to the context of each appointment in seeking responses as feedback from the patients, the healthcare providers, the onsite care coordinators, and the client, and assimilating the information in the client input and the training data. The AORPS 106 analyzes the information and extrapolates the available information in the quest for predicting potential outcomes and impacts from various angles including medical, experiential, and monetary aspects on all stakeholders in the delivery of patient care. The AORPS 106 generates the predictive model and the appointment schedule with travel routes optimally in keeping with stated goals such as the success rate of operation expected by the client as given in the client input and in keeping with implicit goals that are programmed into the algorithms such as maximizing volumes of appointments, minimizing required travel and travel times, and ensuring satisfaction of the stakeholders including the patients. The AORPS 106 ensures satisfaction of the stakeholders in view of the clustering of patients and matching patients with appropriate healthcare providers and onsite care coordinators based on the optimization factors, the dynamic adjusting of the generated appointment schedule with the travel routes with minimum disruption, incorporating feedback received from the stakeholders in generating the predictive model and the appointment schedule, and computing and projecting insurance costs, suitable capitation for the healthcare providers and the onsite care coordinators, and return on investments (ROI) for the client and insurance plans.

As an illustration, in an embodiment, the appointment optimization and route planning system (AORPS) 106 receives client input from a client to obtain the following inputs:
  (a) N number of healthcare providers available on a given day, certain hours a day;
  (b) M number of onsite care coordinators (OCCs) available on a given day, certain hours a day;

(c) The total NH number of healthcare providers hours and NM number of OCC hours available to perform all types of appointments in four groups, that is, G1 to G4, comprising:
only healthcare providers remote;
only OCCs remote;
only OCCs onsite; and healthcare providers remote and OCCs onsite;
(d) A commitment with a health plan to perform a maximum of Z appointments per month with a minimum of X appointments per day, visiting each one of P patients from a cohort at least T times a month; and
(e) Operation at a success rate of at least S (=80% success rate) of covering all appointments per month.

As an example, in an embodiment, the appointment optimization and route planning system (AORPS) 106 performs computation of an input matrix based on input data, comprising:

For every given day from time 0 (today) to 30 days:
(a) creating an input matrix from schedules of the healthcare providers and the onsite care coordinators (OCCs) captured by a computation and ranking engine 220 of the AORPS 106 exemplarily illustrated in FIG. 2C, wherein the schedules of the healthcare providers and the OCCs comprise the combinations—N-G1, NH-G1, N-G3, G4, NH-G3, G4, M-G2, G3, G4, MH-G2, G3, and G4;
(b) planning patient cohorts (P);
(c) computing expectations of minimum daily volume (Xmin) and maximum monthly volume (Zmax); and
(d) computing success rates (S).

An exemplary resulting input matrix is disclosed below:

|  | N-G1 | NH-G1 | N-G3, G4 | NH-G3, G4 | M-G2, G3, G4 | MH-G2, G3, G4 | Z(max) | X(min) | P | T(min) | S |
|---|---|---|---|---|---|---|---|---|---|---|---|
| Day 1 | 2 | 4 | 5 | 8 | 20 | 8 | 150 | 5 | 100 | 1 | 80% |
| Day 2 | 2 | 3 | 5 | 8 | 20 | 8 | 150 | 5 | 100 | 1 | 80% |
| Day 3 | 2 | 6 | 6 | 8 | 25 | 8 | 150 | 5 | 100 | 1 | 80% |
| Day off | 2 |  |  |  |  |  |  |  |  |  |  |
| Day 4 | 2 | 8 | 4 | 8 | 18 | 8 | 150 | 5 | 100 | 1 | 80% |
| ... |  |  |  |  |  |  |  |  |  |  |  |
| Day 30 | 2 | 4 | 5 | 8 | 20 | 8 | 150 | 5 | 100 | 1 | 80% |

An illustration of an algorithm for clustering patients into cohorts based on certain factors is as follows. In this exemplary illustration, the appointment optimization and route planning system (AORPS) 106 clusters the patients into cohorts based on medical conditions, both acute conditions and chronic conditions, language, age, cognitive scores when available, and social determinants of health (SDOH) categories:

Income and social protection
Education
Unemployment and job insecurity
Working life conditions
Food insecurity
Housing, basic amenities, and the environment
Early childhood development
Social inclusion and non-discrimination
Structural conflict
Access to affordable health services of decent quality Moreover, in this exemplary illustration, the appointment optimization and route planning system (AORPS) 106 defines the patient's non-compliance risk clusters, hereinafter referred to as "clusters", by training an embedding model through access to the patient's electronic medical records (EMRs) and obtaining data on non-compliance, as in missed prescriptions, as well as recorded instances for emergency room (ER) visits and hospital admissions/re-admissions. In cases when the data is not available, the AORPS 106 performs the embedding and the training based on a reduced number of dimensions, for example, language, age, and comorbidities, and labeling of data is performed by in-house managed care experts from a healthcare company. In an embodiment, the AORPS 106 computes weights of each vector for embedding the social determinants of health (SDOH) elements using machine learning (ML) algorithms, for example, a linear regression model based on the known risk of SDOH and profile elements for non-compliance or by applying an analytic hierarchy process (AHP) and by computing the ratio of an importance matrix.

Furthermore, in this exemplary illustration, the appointment optimization and route planning system (AORPS) 106 creates geolocated cohorts of similar patients as the patient's non-compliance risk neighborhoods, hereinafter referred to as "neighborhoods", with centroids for each neighborhood, where distance between patients is, for example, within 30 minutes of driving from each other and the neighborhood's centroid is, for example, within 2 hours with traffic, of the onsite care coordinators' reach, either from home or local office. In an embodiment, the AORPS 106 accomplishes geo-clustering as follows. The AORPS 106 iteratively applies filters, where for each patient distance D is, for example, under 60 miles from either an onsite care coordinator's home or local office, and removes patients whose locations by address are at distances in excess of, for example, about 10 miles to about 15 miles, and those that result in a continuously computed centroid for the cluster that is outside of a 60-mile radius. The AORPS 106 computes the centroid as either a minimum distance centroid given by $f(x,y)=\Sigma dk=\Sigma(x_k-x)^2+(y_k-y)^2$, where k=1, or as a moment centroid given by:

$$\bar{x} = \frac{M_y}{A} = \frac{M_{y_1} + M_{y_2} + \cdots + M_{y_N}}{A} = \frac{\sum_{k=1}^{n} A_k \bar{x}_k}{A}$$

and similarly, $$\bar{y} = \frac{\sum_{k=1}^{n} A_k \bar{x}_k}{A}$$

The resulting clusters are the computed neighborhoods. As an example, the AORPS 106 performs the filtering according to the following exemplary pseudocode:

```
neighborhoods = { }
patients = filter (Office location, 60 miles away)
For each patient p do
    Add new neighborhood to neighborhoods
    pool = filter (p, 10 miles away)
    For each pool pn do
        Cp = centroid (pn, neighborhood)
        If (distance (cp, Office location) < 60m)
            Add (pn to neighborhood)
        End
    End
End
```

Figure 2B:
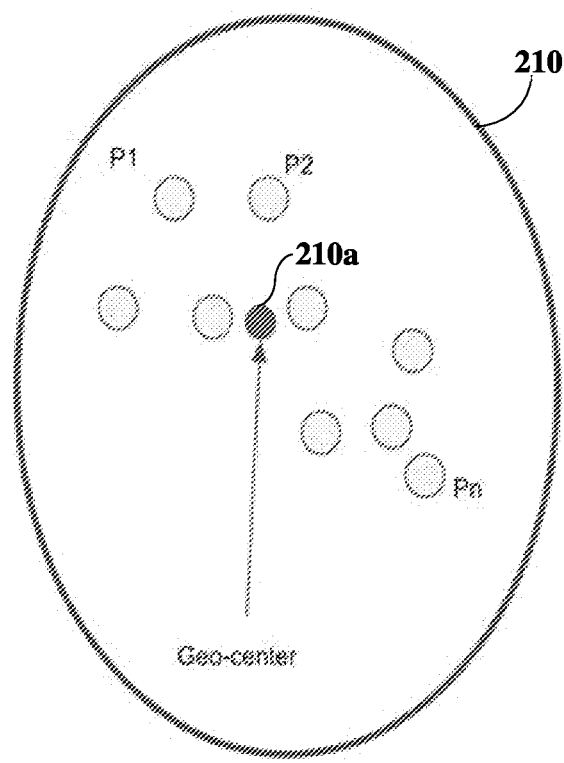
FIG. 2B exemplarily illustrates a pictorial representation of neighborhood clustering performed by an appointment optimization and route planning system for optimizing home-visit appointments and related travel for delivering patient care.

A pictorial representation of neighborhood clustering performed by the appointment optimization and route planning system (AORPS) 106 is exemplarily illustrated in FIG. 2B. In an exemplary illustration, the AORPS 106 prepares categories of appointments for generation of an appointment schedule as follows. For each of the neighborhoods clustered above, for each day of the month, the AORPS 106 computes the following allocations:

MPH: Must-be-seen-at-home patients today—patients that must be seen as it is the last day of the "recommended visit window".

MPT: Must-be-seen-remotely patients today—patients that must be seen as it is the last day of the "recommended visit window".

APH: Acute patient visits at home today based on the percentage of historical neighborhoods acute urgent care visits.

APT: Acute patient visits remotely today based on the percentage of historical neighborhoods acute urgent care visits.

SPH: Should-be-seen-at-home patients today—patients based on the day in the "recommended visit window" range.

SPT: Should-be-seen-remotely patients today—patients based on the day in the "recommended visit window" range.

CPH: Can-be-seen-at-home patients today—patients that must be seen as it is the last day of the "recommended visit window".

CPT: Can-be-seen-remotely patients today—patients based on the day in the "recommended visit window" range.

XP: cancellations based on the percentage of historical neighborhoods' cancellations.

Each of the above categories of appointments comprises the following attributes:

Weight—Appointment Type Weight (ATW), from 1 to 10; and

Priority—Appointment Type Priority (ATP), 0 to 1.

An example of the computed allocations according to the above attributes is disclosed below.

|     | MPH | MPT | APH | APT | SPH | SPT | CPH | CPT |
|-----|-----|-----|-----|-----|-----|-----|-----|-----|
| ATW | 9   | 8   | 10  | 9   | 8   | 7   | 6   | 5   |
| ATP | 0.7 | 0.6 | 0.9 | 0.8 | 0.5 | 0.4 | 0.3 | 0.2 |

In addition to the appointment categories, in an embodiment, the appointment optimization and route planning system (AORPS) 106 computes patient-centric priorities as follows:

Patient Clinical Priority (PCP), 0 to 1, which represents a risk stratification metric representing immediate health or hospitalization-related risk to the patients as a function of time T since the last time the patient was seen; and Patient Financial Priority (PFP), 0 to 1, which represents a risk stratification metric representing the risk of high payments associated with urgent hospital/emergency room (ER) admission or readmission payment as a function of time T since the last time the patient was seen.

Furthermore, in an embodiment, the appointment optimization and route planning system (AORPS) 106 computes total weights of the appointments for a bin packing algorithm by multiplying the Appointment Type Weight (ATW), the Appointment Type Priority (ATP), and a Distance coefficient (Di), where Di is 1 for places 1 mile away from the neighborhood's geo-center, and otherwise, is computed as $(1\div(\text{number of miles from a patient's location to the neighborhood's geo-center}))$. FIG. 2B exemplarily illustrates a geo-center 210a of a neighborhood cluster 210. Each bin in the bin packing algorithm represents either the healthcare providers, or the onsite care coordinators (OCCs), or both depending on the appointment type. The AORPS 106 calculates other parameters as follows:

Single Patient Risk (SPR)=PCP×PFP; and

Single Patient Appointment Weight (SAW) for patient "i"=$ATW_i \times ATP_i \times Di$, where Di is the distance coefficient for each user "i" only for onsite appointments, and is 1 for remote appointments.

As an example, in an embodiment, the appointment optimization and route planning system (AORPS) 106 builds a table with numbers of appointments of each category in each neighborhood as follows:

Neighborhood ID 1 (Zip codes: xxxaa . . . xxxzz)

|         | MPH | MPT | APH | APT | SPH | SPT | CPH | CPT | XP |
|---------|-----|-----|-----|-----|-----|-----|-----|-----|----|
| Day 1   | 3   | 2   | 1   | 1   | 5   | 10  | 15  | 25  | 2  |
| Day 2   | 2   | 1   | 3   | 3   | 2   | 8   | 6   | 15  | 2  |
| Day 3   | 3   | 2   | 1   | 1   | 5   | 10  | 15  | 25  | 2  |
| Day off |     |     |     |     |     |     |     |     |    |
| Day 4   | 2   | 1   | 3   | 3   | 2   | 8   | 6   | 15  | 2  |
| . . .   |     |     |     |     |     |     |     |     |    |
| Day 30  | 3   | 2   | 1   | 1   | 5   | 10  | 15  | 25  | 2  |

The AORPS 106 computes the following two main quantities based on allocation of appointments within the "cluster":

The "Clinical Need for given Neighborhood" (Neighborhood Needs), both minimum and desired; and The "Resource Availability for given Neighborhood" (Neighborhood Availability).

The AORPS 106 computes the Need and Availability quantities separately for the following four appointment types:

Remote with only the healthcare provider;

Remote with only the onsite care coordinator;

At home/onsite with only the onsite care coordinator; and

At home/onsite with the onsite care coordinator while the healthcare provider is remote.

In each category, Availability should be equal to or greater than Need, and overall, depends on the constraints of a finite number of available hours for the healthcare providers and the onsite care coordinators (OCC) per day. In an example, the AORPS 106 computes Need and Availability as follows:

Neighborhood Need (All appointments planned for each Neighborhood per Day)=$\Sigma_{all\ at\ home}SAW_i$+ $\Sigma_{all\ remote}SAW_j$+$\Sigma_{all\ provider-only}SAW_k$+ $\Sigma_{all\ assistance}SAW_l$ Neighborhood Availability=$\Sigma_{all\ at-home}Capacity_i$++ $\Sigma$remote Capacity$_j$+$\Sigma_{all\ provider-only}Capacity_k$+ $\Sigma_{all\ assistance}Capacity_l$ Where, SAW is the Single Patient Appointment Weight.

In an exemplary illustration, the appointment optimization and route planning system (AORPS) 106 generates an appointment schedule as an Appointments Matrix using an algorithm as follows. For every patient, at the time of the Appointments Matrix initial construction or every subsequent reconstruction, the AORPS 106 recomputes Single Patient Risk (SPR). For each of the backlog appointments, the AORPS 106 adds 0.1 to the Appointment Type Priority (ATP). Moreover, the AORPS 106 recomputes every Single Patient Appointment Weight (SAW). The AORPS 106 then ranks all planned patients' appointment visits for the next 24 hours by Single Patient Appointment Weight (SAW), and fills up the Appointment Matrix's day, leaving empty spaces for hours where personnel are not available. The AORPS 106 adjusts time slots that have been rejected by patients and retains previously reserved slots that have been confirmed by patients. The AORPS 106 allocates the appointments within each of the four appointment types until available resources are exhausted in each group and places the rest of the appointments into a backlog 226 as exemplarily illustrated in FIG. 2C. In an embodiment, the AORPS 106 allocates the appointments for each of the neighborhoods using a bin-packing algorithm or a bin-packing with priorities algorithm for each day, forming a rolling monthly matrix of appointments for each client, herein exemplarily referred to as a 30-day Matrix or 30D-Matrix. The AORPS 106 optimizes the sequence of appointments by clustering together appointments by geo-proximity for groups of appointments with similar SAW ranking score. The AORPS 106 uses deep learning or machine learning (ML) techniques that allow the building of the most optimal daily schedule by applying specific techniques for onsite versus remote appointments.

Figure 2C:
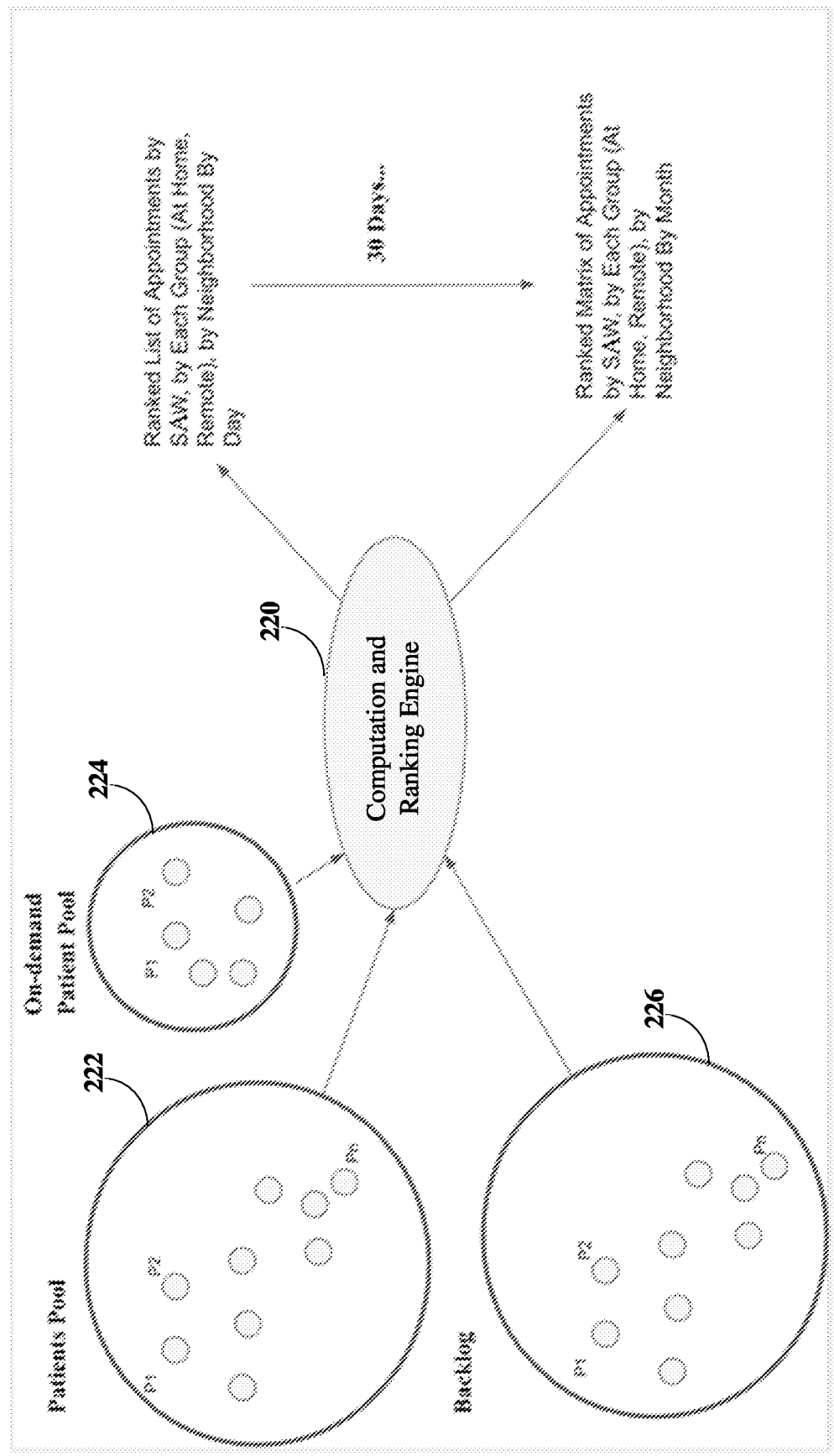
FIG. 2C exemplarily illustrates operations of a computing and ranking engine in the appointment optimization and route planning system for optimizing home-visit appointments and related travel for delivering patient care.

FIG. 2C exemplarily illustrates operations of the computing and ranking engine 220 in the appointment optimization and route planning system (AORPS) 106 shown in FIG. 1, for optimizing home-visit appointments and related travel for delivering patient care. The computation and ranking engine 220 of the AORPS 106 utilizes a patients pool 222, an on-demand patient pool 224, and the backlog 226 as input and generates a ranked list of appointments, for example, by the single patient appointment weight (SAW), by each group at home or remote, and by neighborhood by day. The computation and ranking engine 220 also generates a ranked matrix of appointments, for example, by SAW, by each group, and by neighborhood by month.

In contrast to conventional systems that use particle swarm optimization (PSO) to address a bin packing problem and methods to assign different operations to periods and resources, considering resources' compatibilities and due dates, the algorithm executed by the AORPS 106 ties dynamic risk computation to plan financial exposure, patients' health risks, as well as each individual patient's social determinants of health and combination of onsite and off-site visits as the basis of artificial intelligence-based and machine learning-based optimization algorithms, and the bin packing with priorities algorithm is executed as a part of the stack. A pseudocode illustrating the computations executed by the AORPS 106 is disclosed below.

```
For i = 1 to 30 do
    Read Backlog
    Recompute ATP
    Recompute SPR
    Recompute SAW
    Compute resources available for the next 24 hours
    Allocate appointments from ranked list in 4 types
END
```

On the very first computation of the 30-day Matrix (30D-Matrix), the appointment scheduling modules 102, in communication with the appointment optimization and route planning system (AORPS) 106, send appointment invitations to all the patients, the healthcare providers, and the onsite coordinators. The AORPS 106 requests those that reject or would like to reschedule, to reschedule based on a current state of capacity calendars. The AORPS 106, via the appointment scheduling modules 102, sends reminders to those who did not reply to the appointment invitations, for example, for a total of two weeks, once a week, by a call, or an email, or both, and in case of no reply, removes them from the planner and sends them to the client's resources to schedule the visit manually. This process optimizes each individual neighborhood's 30D-Matrix and then optimizes performance across all neighborhoods.

In an exemplary illustration, the appointment optimization and route planning system (AORPS) 106 optimizes the appointment schedule generated as an Appointments Matrix as follows. The AORPS 106 populates the Appointments Matrix for each of the neighborhoods daily, for example, for the next 30 days, with day-by-day processing, planning one day at a time, with only "local optimization", that is, "single day optimization", and with the understanding that after the generation of the appointment schedule, the AORPS 106 will optimize the Appointments Matrix. Once the AORPS 106 computes the Appointments Matrix, the AORPS 106 computes a Total Appointment Allocation number, which represents the total predicted number of planned visits for a population of P patients with a maximum 30-day appointment count Zmax and a success rate of at least S as determined by the client across each of the neighborhoods. The AORPS 106 also computes Neighborhood Population Risk (NPR), which represents the health risk and financial exposure for a given neighborhood, as follows:

Neighborhood Population Risk (NPR)= $\Sigma_{all\ patients}SPR_i$

The appointment optimization and route planning system (AORPS) 106 optimizes the computed Neighborhood Population Risk (NPR) by applying variants of the bin packing and the bin packing with priorities algorithms, and proceeds to optimize the non-yet-confirmed or not-yet-planned appointments for NPR on the level of the entire neighborhood. The appointment scheduling modules 102, in communication with the AORPS 106, sends out updated appointment invitations for all changes that result in the Appointments Matrix due to newly rescheduled appointments. After the individual optimization for each of the neighborhood's NPR, the AORPS 106 performs a computation to check whether there are any further available resources, that is, healthcare providers and/or onsite care coordinators (OCCs), for each day, and computes a Neighborhood Available Buffer Matrix, which can be applied to other neighborhoods with centroids that are under 10 miles away. The optimization for all neighborhoods starts with ranking of all neighborhoods by their cumulative NPR and then executing the optimization linearly starting with the largest NPR, where each subsequent neighborhood receives the previously computed Neighborhood Available Buffer Matrix.

Figure 3:
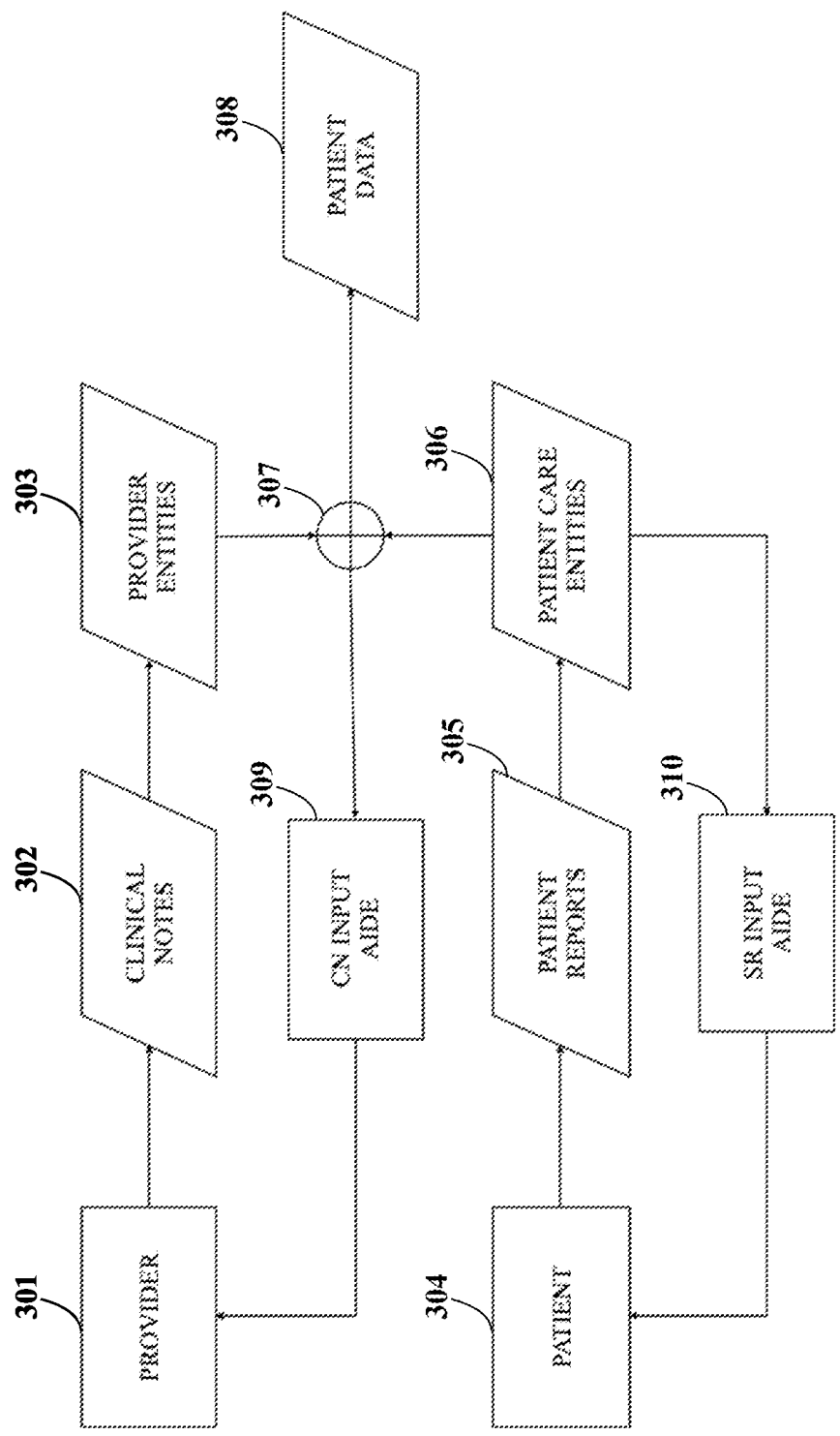
FIG. 3 exemplarily illustrates a flow diagram indicating a flow of data for forming patient data received by the appointment optimization and route planning system.

FIG. 3 exemplarily illustrates a flow diagram indicating a flow of data for forming patient data received by the appointment optimization and route planning system (AORPS) 106 shown in FIG. 1. A provider 301 who provides healthcare to patients compiles clinical notes 302 comprising, for example, diagnoses, lab test recommendations, prescriptions, response of patients to medication, recuperation progress of patients, and other patient care information. The clinical notes 302 are accessible to provider entities 303 such as healthcare providers who administer programs such as urgent care on demand, a primary care provider (PCP) program, and/or a chronic care management (CCM) program for patients and organizations that manage medical records and related patient care data. A patient 304 possesses patient reports 305 of diagnoses and visits to different doctors and other medical practitioners. A patient 304 is best suited to provide a first-hand, self-report of symptoms, medical conditions, effects of medication and/or therapy, and recuperation progress when recovering from illnesses. As such, the patient reports 305 further comprise lab reports and self-reports from the patient 304. Patient care entities 306 have access to the patient reports 305 of patients under their care or management. A healthcare company that avails the services of the AORPS 106 and has at least one administrator as a client for the AORPS 106 is an example of a patient care entity 306. Patient care entities 306 further comprise individuals or organizations, for example, independent physician associations (IPAs) and accountable care organizations (ACOs). The AORPS 106 receives the clinical notes 302 from the provider entities 303 and the patient reports 305 from the patient care entities 306 as part of patient data.

As disclosed in the description of FIG. 1, the data reception module 106a of the appointment optimization and route planning system (AORPS) 106 exemplarily illustrated in FIG. 1, communicates with the patients, the client, the healthcare providers, and the onsite care coordinators through the appointment scheduling modules 102 via the network 118. The data reception module 106a provides a web interface or a mobile app interface on the appointment scheduling modules 102 for facilitating the communication. An aggregation component 307 of the data reception module 106a aggregates the clinical notes 302 from the provider entities 303 and the patient reports 305 from the patient care entities 306. The data reception module 106a provides the web interface or the mobile app interface on the appointment scheduling modules 102 as a computer-aided interface with algorithms to match user-provided data with standard ontologies of health-related information in real time and provide input suggestions while receiving input as disclosed in the description of FIG. 1. While aggregating the data being received through the aggregation component 307, the data reception module 106a provides input suggestions via the computer-aided interface in the form of a clinical notes (CN) input aide 309 to the provider 301 and in the form of a self report (SR) input aide 310 to the patient 304. The resulting feedback loops with the provider 301 and the patient 304 ensures parity in the structure and composition of data received from different providers 301 and patients 304. The resulting aggregated data from the aggregation component 307 forms patient data 308 that the data reception module 106a of the AORPS 106 receives. The input processing module 106b of the AORPS 106 exemplarily illustrated in FIG. 1, then handles the received patient data 308 to collate the received patient data 308 as disclosed in the description of FIG. 1. The aggregation component 307 also aggregates other data (not shown) that the data reception module 106a receives from the patients, the client, the healthcare providers, the onsite care coordinators, and trusted sources 120 exemplarily illustrated in FIG. 1, including the client input, availability of the patients, the healthcare providers, and the onsite care coordinators in a schedule, feedback that forms a part of training data for the predictive model, and healthcare data from the trusted sources 120 as disclosed in the description of FIG. 1.

Figure 4:
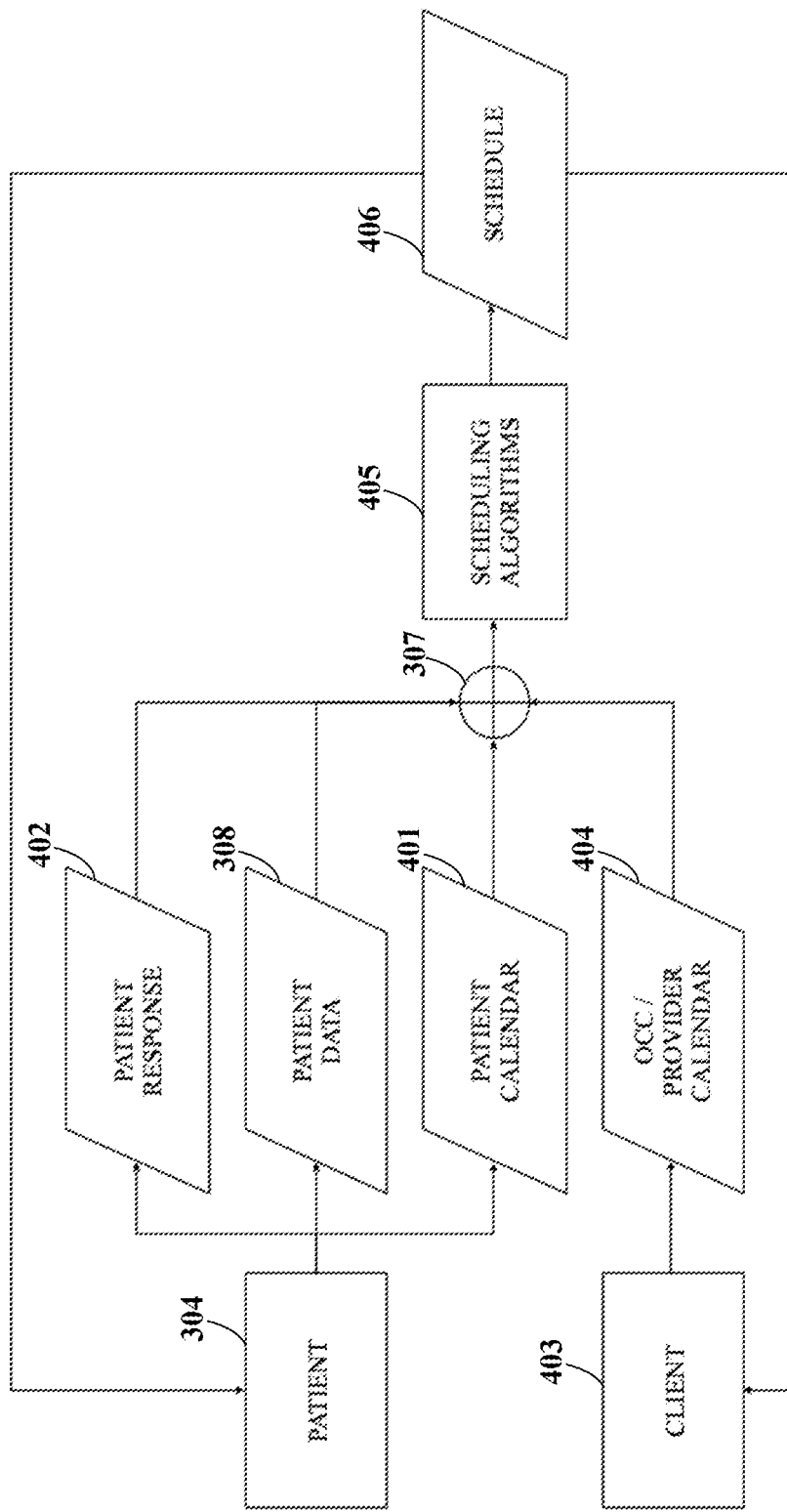
FIG. 4 exemplarily illustrates a flow diagram indicating a flow of data for forming an appointment schedule dynamically generated by the appointment optimization and route planning system.

FIG. 4 exemplarily illustrates a flow diagram indicating a flow of data for forming an appointment schedule dynamically generated by the appointment optimization and route planning system (AORPS) 106 shown in FIG. 1. As disclosed in the descriptions of FIG. 3 and FIG. 1, the aggregation component 307 which is a part of the data reception module 106a exemplarily illustrated in FIG. 1, aggregates data from a provider 301 and a patient 304 via the provider entities 303 and the patient care entities 306 exemplarily illustrated in FIG. 3, (connections not shown in FIG. 4), to result in patient data 308. The aggregation component 307 aggregates the previously resulting patient data 308 with other data comprising, for example, availability of the patient 304 for a home-visit appointment from a patient calendar 401 and hours of availability of onsite care coordinators (OCCs) and healthcare providers from an OCC/provider calendar 404. As disclosed in the description of FIG. 1, the data reception module 106a receives the hours of availability of the OCCs and the healthcare providers as part of the client input from a client 403, for example, an administrator of a healthcare company, using a client device 119 exemplarily illustrated in FIG. 1, or another electronic device that communicates with the data reception module 106a through a web or a mobile app interface on the appointment scheduling modules 102 exemplarily illustrated in FIG. 1. Moreover, the data reception module 106a receives confirmation of acceptance or rejection of a scheduled appointment as a patient response 402 that feeds into the aggregation component 307. The resulting data from the aggregation component 307 is sent to scheduling algorithms 405 that form part of the input processing module 106b and the output generation module 106c exemplarily illustrated in FIG. 1.

As disclosed in the description of FIG. 1, the input processing module 106b collates the patient data 308, generates an input matrix, and passes on the collated patient data and the generated input matrix to the output generation module 106c. The output generation module 106c uses the collated patient data, the client input from the client 403, the generated input matrix (not shown), healthcare data (not shown), and a predictive model (not shown) that the output generation module 106c generates, to generate a schedule 406 as an appointment schedule along with travel routes dynamically based on optimization factors. The output generation module 106c sends the generated schedule 406 to the client 403 and in turn, to the healthcare providers and the onsite care coordinators, and to the patient 304 to indicate an appointment date and time for a home-visit for patient care. The patient 304 and the client 403, in turn, provide the patient response 402 and any changes to the onsite care coordinator (OCC)/provider calendar 404, respectively, as feedback that is incorporated into the generation of the schedule 406 in real time to dynamically adjust the schedule 406 if necessary. The flow diagram in FIG. 4 exemplarily illustrates, in a focused manner, the flow of data from the patient 304 and the client 403 with feedback for the generation of the schedule 406 by the scheduling algorithms 405 as a high-level flow diagram abstracting other data, such as, the generated input matrix, the healthcare data, and the predictive model that also form inputs in the generation of the schedule 406.

The non-transitory, computer-readable storage medium, for example, the memory unit 105 in the system 100 exemplarily illustrated in FIG. 1, stores computer program codes comprising instructions executable by at least one processor 107 for optimizing home-visit appointments and related travel for delivering patient care. The computer program codes comprise a first computer program code for receiving registration data and patient data from patients, wherein the patient data comprises age, gender, profession, location, lists of chronic health conditions, medical history, healthcare programs enrolled by the patients, free-form self-reports about current health, reasons for requiring medical attention, preferred time bounds to interact with one or more of the healthcare providers and the onsite care coordinators, and payment information; a second computer program code for receiving client input comprising hours of availability of healthcare providers and onsite care coordinators, appointment types, health plan commitments, and a success rate of operation, from a client; a third computer program code for collating the received patient data; a fourth computer program code for generating an input matrix based on the received client input and the collated patient data, covering a preconfigured period of time, for example, thirty days, wherein the input matrix comprises schedules of the healthcare providers and the onsite care coordinators, patient cohorts, expected minimum daily and maximum monthly volumes of appointments, and success rates; a fifth computer program code for generating a predictive model based on training data comprising appointment history, patient history, feedback, and healthcare data, wherein the healthcare data comprises healthcare information of cohorts similar to the patients in terms of demographics and comorbidities, costs of healthcare implementations in a country, and insurance information, and wherein the predictive model comprises predicted patient behaviors, suggested cadence of appointments for each of the patients, predicted equipment requirements, appointment cancellation probabilities for each of the patients, potential outcomes, expected costs, capitation projections for insurance plans, return on investment (ROI) for the insurance plans, and clusters of patients based on each of the collated patient data, the client input, the feedback in the training data, social and psychosocial determinants of health of the patients, insurance plans of the patients, and insurance plan needs of the patients; and a sixth computer program code for generating an appointment schedule with travel routes dynamically based on optimization factors derived from the received client input, the collated patient data, the generated input matrix, the healthcare data, and the generated predictive model, via a mapping using the global navigation satellite system (GNSS) module 103 exemplarily illustrated in FIG. 1, incorporating real-time changes in the patient data, the client input, the optimization factors, and appointments.

The non-transitory, computer-readable storage medium disclosed herein further stores additional computer program codes for performing additional steps that may be required and contemplated for optimizing home-visit appointments and related travel for delivering patient care. In an embodiment, a single piece of computer program code comprising computer executable instructions performs one or more steps of the computer-implemented method disclosed herein for optimizing home-visit appointments and related travel for delivering patient care. The computer program codes comprising computer executable instructions are embodied on the non-transitory, computer-readable storage medium. The processor 107 of the system 100 retrieves these computer executable instructions and executes them. When the computer executable instructions are executed by the processor 107, the computer executable instructions cause the processor 107 to perform the steps of the computer-implemented method for optimizing home-visit appointments and related travel for delivering patient care.

In the computer-implemented method disclosed herein, the design and flow of interactions between the appointment optimization and route planning system (AORPS) 106 and the rest of the system 100 comprising the appointment scheduling modules 102, the mapping module 104, and the GNSS module 103, and with the client device 119 provided to the client, electronic devices of the patients, the healthcare providers, and the onsite care coordinators, and the trusted sources 120 via the network 118 exemplarily illustrated in FIG. 1, are deliberate, designed, and directed. The interactions designed by the AORPS 106 allow the AORPS 106 to obtain patient data from electronic devices of the patients, client input from the client device 119 or an electronic device of the client, healthcare data from the trusted sources 120, and availability for home-visit appointments and feedback from the patients, the healthcare providers, and the onsite care coordinators. From the patient data, the client input, the healthcare data, and the feedback, through the use of other separate and autonomous computer programs that employ one or more of decision trees, regression models, machine learning, and artificial intelligence, the input processing module 106b and the output generation module 106c of the AORPS 106 transform data, generate intelligent outputs, generate statistical predictions through a predictive model, and dynamically alter the generated outputs in real time based on feedback and new or changed inputs.

The input processing module 106b transforms raw information that the patients, the client, the healthcare providers, and the onsite care coordinators input to the appointment optimization and route planning system (AORPS) 106 by providing input suggestions for compatibility of received patient data and feedback with standard ontologies of health-related information, collating patient data encompassing a wide variety of aspects of personality and patient care, and generating an input matrix to yield coherence of client input and possible appointments. The output generation module 106c creates a feedback loop to generate a predictive model to predict a range of outcomes from capitation projections to patient behaviors. Moreover, the output generation module 106c takes into account information from different fronts as optimization factors to intelligently and dynamically optimize aspects of patient care from matching patients to appropriate healthcare personnel to minimizing driving distances with real-time adjustments.

The appointment optimization and route planning system (AORPS) 106 executes autonomous computer programs defined by artificial intelligence, machine learning, regression models, and decision trees to optimizing home-visit appointments and related travel for delivering patient care with up-to-date references in prevailing standards of healthcare. To provide input suggestions by using natural language processing (NLP) and matching input to standard ontologies in healthcare, collate patient data that is comprehensive, generate a cohesive input matrix clarifying goals, generate and update a practically useful predictive model, and dynamically generate a comprehensively optimized appointment schedule and travel routes that are responsive to real-time changes require more than five (5) separate computer programs, the execution of which cannot be easily or manually executed by a person working with a generic computer. A generic computer using a generic program cannot collate wide-ranging data in accordance with standard ontologies in healthcare, predict patient behaviors and probabilities of cancellation of appointments, receive feedback by intelligently posing relevant questions and prompts, and dynamically generate an appointment schedule with optimal travel routes that is optimized over multiple disparate factors and that remains responsive in real time to changes in accordance with the method steps disclosed above.

It is readily apparent in different embodiments that the various methods, algorithms, and computer-readable programs disclosed herein are implemented on non-transitory, computer-readable storage media appropriately programmed for computing devices. The non-transitory, computer-readable storage media participate in providing data, for example, instructions that are read by a computer, a processor, or a similar device. In different embodiments, the "non-transitory, computer-readable storage media" also refers to a single medium or multiple media, for example, a centralized database, a distributed database, and/or associated caches and servers that store one or more sets of instructions that are read by a computer, a processor, or a similar device. The "non-transitory, computer-readable storage media" also refer to any medium capable of storing or encoding a set of instructions for execution by a computer, a processor, or a similar device and that causes a computer, a processor, or a similar device to perform any one or more of the methods disclosed herein.

In an embodiment, the computer programs that implement the methods and algorithms disclosed herein are stored and transmitted using a variety of media, for example, the computer-readable media in various manners. In an embodiment, hard-wired circuitry or custom hardware is used in place of, or in combination with, software instructions for implementing the processes of various embodiments. Therefore, the embodiments are not limited to any specific combination of hardware and software. The computer program codes comprising computer executable instructions can be implemented in any programming language. Examples of programming languages that can be used comprise C, C++, C#, Java®, JavaScript®, Fortran, Ruby, Perl®, Python®, Visual Basic®, hypertext preprocessor (PHP), Microsoft®.NET, Objective-C®, etc. Other object-oriented, functional, scripting, and/or logical programming languages can also be used. In an embodiment, the computer program codes or software programs are stored on or in one or more mediums as object code. In another embodiment, various aspects of the system and the computer-implemented method disclosed herein are implemented in a non-programmed environment comprising documents created, for example, in a hypertext markup language (HTML), an extensible markup language (XML), or other format that render aspects of a graphical user interface (GUI) or perform other functions, when viewed in a visual area or a window of a browser program. In another embodiment, various aspects of the system and the computer-implemented method disclosed herein are implemented as programmed elements, or non-programmed elements, or any suitable combination thereof.

Where databases are described such as the database(s) 106d, it will be understood by one of ordinary skill in the art that (i) alternative database structures to those described may be employed, and (ii) other memory structures besides databases may be employed. Any illustrations or descriptions of any sample databases disclosed herein are illustrative arrangements for stored representations of information. In an embodiment, any number of other arrangements are employed besides those suggested by tables illustrated in the drawings or elsewhere. Similarly, any illustrated entries of the databases represent exemplary information only; one of ordinary skill in the art will understand that the number and content of the entries can be different from those disclosed herein. In another embodiment, despite any depiction of the databases as tables, other formats comprising relational databases, object-based models, and/or distributed databases are used to store and manipulate the data types disclosed herein. Object methods or behaviors of a database can be used to implement various processes such as those disclosed herein. In another embodiment, the databases are, in a known manner, stored locally or remotely from a device that accesses data in such a database. In embodiments where there are multiple databases in the system, the databases are integrated to communicate with each other for enabling simultaneous updates of data linked across the databases, when there are any updates to the data in one of the databases.

The system and the computer-implemented method disclosed herein can be configured to work in a network environment comprising one or more computers that are in communication with one or more devices via a network. In an embodiment, the computers communicate with the devices directly or indirectly, via a wired medium or a wireless medium such as the Internet, a local area network (LAN), a wide area network (WAN) or the Ethernet, a token ring, or via any appropriate communications mediums or combination of communications mediums. Each of the devices comprises processors, examples of which are disclosed above, that are adapted to communicate with the computers. In an embodiment, each of the computers is equipped with a network communication device, for example, a network interface card, a modem, or other network connection device suitable for connecting to a network. Each of the computers and the devices executes an operating system, examples of which are disclosed above. While the operating system may differ depending on the type of computer, the operating system provides the appropriate communications protocols to establish communication links with the network. Any number and type of machines may be in communication with the computers.

The system and the computer-implemented method disclosed herein are not limited to a particular computer system platform, processor, operating system, or network. In an embodiment, one or more aspects of the system and the computer-implemented method disclosed herein are distributed among one or more computer systems, for example, servers configured to provide one or more services to one or more client computers, or to perform a complete task in a distributed system. For example, one or more aspects of the system and the computer-implemented method disclosed herein are performed on a client-server system that comprises components distributed among one or more server systems that perform multiple functions according to various embodiments. These components comprise, for example, executable, intermediate, or interpreted code, which communicate over a network using a communication protocol. The system and the computer-implemented method disclosed herein are not limited to be executable on any particular system or group of systems, and are not limited to any particular distributed architecture, network, or communication protocol.

The foregoing examples and illustrative implementations of various embodiments have been provided merely for explanation and are in no way to be construed as limiting of the system and the computer-implemented method disclosed herein. While the system and the computer-implemented method have been described with reference to various embodiments, it is understood that the words, which have been used herein, are words of description and illustration, rather than words of limitation. Further, although the system and the computer-implemented method have been described herein with reference to particular means, materials, techniques, and embodiments, the system and the computer-implemented method are not intended to be limited to the particulars disclosed herein; rather, the system and the computer-implemented method extend to all functionally equivalent structures, methods and uses, such as are within the scope of the appended claims. While multiple embodiments are disclosed, it will be understood by those skilled in the art, having the benefit of the teachings of this specification, that the system and the computer-implemented method disclosed herein are capable of modifications and other embodiments may be effected and changes may be made thereto, without departing from the scope and spirit of the system and the computer-implemented method disclosed herein.

We claim:

1. A system for optimizing home-visit appointments and related travel for delivering patient care, the system comprising:
   one or more appointment scheduling modules;
   a global navigation satellite system module;
   a mapping module configured to receive location input from the global navigation satellite system module;
   a non-transitory, computer-readable storage medium configured to store computer program instructions and data defined by an appointment optimization and route planning system;
   at least one processor communicatively coupled to the non-transitory, computer-readable storage medium, the at least one processor configured to execute the defined computer program instructions; and
   the appointment optimization and route planning system comprising:
      a data reception module configured to receive registration data and patient data from patients;
      the data reception module further configured to receive client input comprising hours of availability of healthcare providers and onsite care coordinators, appointment types, health plan commitments, and a success rate of operation, from a client;
      an input processing module configured to collate the received patient data;
      the input processing module further configured to generate an input matrix based on the received client input and the collated patient data, covering a preconfigured period of time, the input matrix comprising schedules of the healthcare providers and the onsite care coordinators, patient cohorts, expected minimum daily and maximum monthly volumes of appointments, and success rates of the appointments;
      an output generation module configured to generate a predictive model based on training data comprising appointment history, patient history, feedback, and healthcare data; and
      the output generation module further configured to generate an appointment schedule with travel routes dynamically via the mapping module using the global navigation satellite system module based on optimization factors derived from the received client input, the collated patient data, the generated input matrix, the healthcare data, and the generated predictive model, incorporating real-time changes in the patient data, the client input, the optimization factors, and appointments.

2. The system of claim 1, further comprising a client device configured for use by the client to communicate with the one or more appointment scheduling modules via a network.

3. The system of claim 1, wherein the output generation module of the appointment optimization and route planning system is configured to utilize one or more of decision trees, machine learning models, and regression models for generating and executing the predictive model and for generating the appointment schedule.

4. The system of claim 1, wherein the received patient data comprises age, gender, profession, location, lists of chronic health conditions, medical history, healthcare programs enrolled by the patients, free-form self-reports about current health, reasons for requiring medical attention, preferred time bounds to interact with one or more of the healthcare providers and the onsite care coordinators, and payment information.

5. The system of claim 1, wherein the data reception module is further configured to match input from the patients, while receiving the patient data, with standard ontologies of health-related information in real time to provide input suggestions to the patients while receiving the patient data.

6. The system of claim 1, wherein the data reception module is further configured to receive the feedback in the training data from the patients, the client, the healthcare providers, and the onsite care coordinators.

7. The system of claim 1, wherein the healthcare data comprises healthcare information of cohorts similar to the patients in terms of demographics and comorbidities, costs of healthcare implementations in a country, and insurance information.

8. The system of claim 1, wherein the predictive model comprises predicted patient behaviors, suggested cadence of appointments for each of the patients, predicted equipment requirements, appointment cancellation probabilities for each of the patients, potential outcomes, expected costs, capitation projections for insurance plans, return on investment for the insurance plans, and clusters of patients based on each of the collated patient data, the client input, the feedback in the training data, social and psychosocial determinants of health of the patients, insurance plans of the patients, and insurance plan needs of the patients.

9. The system of claim 1, wherein the output generation module of the appointment optimization and route planning system is further configured to assign a mode of appointment comprising one of a remote, high-touch patient examination mode and a telehealth mode to each of the appointments in the generated appointment schedule based on the optimization factors.

10. The system of claim 1, wherein the output generation module of the appointment optimization and route planning system is further configured to dynamically adjust the generated appointment schedule with the travel routes in real time based on changes in the optimization factors, changes in the patients, changes in the healthcare providers and the onsite care coordinators, and rejection of the appointments by the patients with minimal disruption.

11. A computer-implemented method employing an appointment optimization and route planning system configured to define computer program instructions executable by at least one processor for optimizing home-visit appointments and related travel for delivering patient care, the method comprising:
receiving registration data and patient data from patients;
receiving client input comprising hours of availability of healthcare providers and onsite care coordinators, appointment types, health plan commitments, and a success rate of operation, from a client;
collating the received patient data;
generating an input matrix based on the received client input and the collated patient data, covering a preconfigured period of time, the input matrix comprising schedules of the healthcare providers and the onsite care coordinators, patient cohorts, expected minimum daily and maximum monthly volumes of appointments, and success rates of the appointments;
generating a predictive model based on training data comprising appointment history, patient history, feedback, and healthcare data; and
generating an appointment schedule with travel routes dynamically based on optimization factors derived from the received client input, the collated patient data, the generated input matrix, the healthcare data, and the generated predictive model, incorporating real-time changes in the patient data, the client input, the optimization factors, and appointments, via a mapping using a global navigation satellite system module.

12. The computer-implemented method of claim 11, wherein the generation and execution of the predictive model and the generation of the appointment schedule is performed by utilizing one or more of decision trees, machine learning models, and regression models.

13. The computer-implemented method of claim 11, wherein the received patient data comprises age, gender, profession, location, lists of chronic health conditions, medical history, healthcare programs enrolled by the patients, free-form self-reports about current health, reasons for requiring medical attention, preferred time bounds to interact with one or more of the healthcare providers and the onsite care coordinators, and payment information.

14. The computer-implemented method of claim 11, further comprising matching input from the patients, while receiving the patient data, with standard ontologies of health-related information in real time to provide input suggestions to the patients while receiving the patient data.

15. The computer-implemented method of claim 11, further comprising receiving the feedback in the training data from the patients, the client, the healthcare providers, and the onsite care coordinators.

16. The computer-implemented method of claim 11, wherein the healthcare data comprises healthcare information of cohorts similar to the patients in terms of demographics and comorbidities, costs of healthcare implementations in a country, and insurance information.

17. The computer-implemented method of claim 11, wherein the predictive model comprises predicted patient behaviors, suggested cadence of appointments for each of the patients, predicted equipment requirements, appointment cancellation probabilities for each of the patients, potential outcomes, expected costs, capitation projections for insurance plans, return on investment for the insurance plans, and clusters of patients based on each of the collated patient data, the client input, the feedback in the training data, social and psychosocial determinants of health of the patients, insurance plans of the patients, and insurance plan needs of the patients.

18. The computer-implemented method of claim 11, further comprising assigning a mode of appointment comprising one of a remote, high-touch patient examination mode and a telehealth mode to each of the appointments in the generated appointment schedule based on the optimization factors.

19. The computer-implemented method of claim 11, further comprising dynamically adjusting the generated appointment schedule with the travel routes in real time based on changes in the optimization factors, changes in the patients, changes in the healthcare providers and the onsite care coordinators, and rejection of the appointments by the patients with minimal disruption.

20. A non-transitory, computer-readable storage medium having embodied thereon, computer program codes comprising instructions executable by at least one processor for optimizing home-visit appointments and related travel for delivering patient care, the computer program codes comprising:
a first computer program code for receiving registration data and patient data from patients, wherein the patient data comprises age, gender, profession, location, lists of chronic health conditions, medical history, healthcare programs enrolled by the patients, free-form self-reports about current health, reasons for requiring medical attention, preferred time bounds to interact with one or more of the healthcare providers and the onsite care coordinators, and payment information;
a second computer program code for receiving client input comprising hours of availability of healthcare providers and onsite care coordinators, appointment types, health plan commitments, and a success rate of operation, from a client;
a third computer program code for collating the received patient data;
a fourth computer program code for generating an input matrix based on the received client input and the collated patient data, covering a preconfigured period of time, the input matrix comprising schedules of the healthcare providers and the onsite care coordinators, patient cohorts, expected minimum daily and maximum monthly volumes of appointments, and success rates of the appointments;
a fifth computer program code for generating a predictive model based on training data comprising appointment history, patient history, feedback, and healthcare data, wherein the healthcare data comprises healthcare information of cohorts similar to the patients in terms of demographics and comorbidities, costs of healthcare implementations in a country, and insurance information, and wherein the predictive model comprises predicted patient behaviors, suggested cadence of appointments for each of the patients, predicted equipment requirements, appointment cancellation probabilities for each of the patients, potential outcomes, expected costs, capitation projections for insurance plans, return on investment for the insurance plans, and clusters of patients based on each of the collated patient data, the client input, the feedback in the training data, social and psychosocial determinants of health of the patients, insurance plans of the patients, and insurance plan needs of the patients; and
a sixth computer program code for generating an appointment schedule with travel routes dynamically based on optimization factors derived from the received client input, the collated patient data, the generated input matrix, the healthcare data, and the generated predictive model, via a mapping using a global navigation satellite system module, incorporating real-time changes in the patient data, the client input, the optimization factors, and appointments.

\* \* \* \* \*